(12) United States Patent
Hayakawa

(10) Patent No.: US 8,545,457 B2
(45) Date of Patent: Oct. 1, 2013

(54) SPRAYER

(75) Inventor: Koichi Hayakawa, Tokyo (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 1252 days.

(21) Appl. No.: 12/265,498

(22) Filed: Nov. 5, 2008

(65) Prior Publication Data

US 2009/0124986 A1 May 14, 2009

(30) Foreign Application Priority Data

Nov. 8, 2007 (JP) ................................ 2007-291349
Mar. 7, 2008 (JP) ................................ 2008-057965

(51) Int. Cl.
*A61B 19/00* (2006.01)

(52) U.S. Cl.
USPC ........................... 604/240; 604/197; 606/214

(58) Field of Classification Search
USPC ............. 604/23–24, 126, 181, 187–188, 191, 604/236, 262, 272–274, 290; 239/8; 95/46
See application file for complete search history.

(56) References Cited

U.S. PATENT DOCUMENTS

| | | | |
|---|---|---|---|
| 3,976,529 A * | 8/1976 | Weichselbaum | 156/272.4 |
| 4,400,168 A * | 8/1983 | Buechel et al. | 604/48 |
| 4,846,405 A | 7/1989 | Zimmermann | |
| 4,924,570 A * | 5/1990 | Mizrah et al. | 29/896.62 |
| 5,755,362 A | 5/1998 | Rodriguez, Jr. et al. | |
| 5,873,918 A * | 2/1999 | Dillman et al. | 55/282.3 |
| 5,902,747 A * | 5/1999 | Nemser et al. | 435/325 |
| 6,102,976 A * | 8/2000 | Oji et al. | 55/282.3 |
| 6,165,201 A * | 12/2000 | Sawhney et al. | 606/214 |
| 6,458,147 B1 * | 10/2002 | Cruise et al. | 606/214 |
| 6,464,663 B1 | 10/2002 | Zinger | |
| 6,494,938 B2 * | 12/2002 | Sims et al. | 96/6 |
| 6,949,132 B2 * | 9/2005 | Thielen et al. | 96/6 |
| 7,144,443 B2 * | 12/2006 | Gerner et al. | 95/46 |
| 7,713,331 B2 * | 5/2010 | Gerner et al. | 95/46 |
| 2003/0187408 A1 | 10/2003 | Marx | |

(Continued)

FOREIGN PATENT DOCUMENTS

EP  1 955 660 A2  8/2008
GB  1 221 625  2/1971

(Continued)

OTHER PUBLICATIONS

Extended European Search Report issued in corresponding EP 08 16 8525, Jan. 27, 2009; EPO, Munich, DE.

(Continued)

*Primary Examiner* — Leslie Deak
*Assistant Examiner* — Sara Sass
(74) *Attorney, Agent, or Firm* — Buchanan Ingersoll & Rooney PC

(57) ABSTRACT

A sprayer which inhibits or prevents clogging from occurring in a nozzle when a liquid is ejected from the nozzle includes a nozzle having a first internal tube through which a first liquid passes, and a second internal tube through which a second liquid passes. An external tube is provided in which the first internal tube and the second internal tube are positioned so that the gas passes therebetween. In the sprayer, each distal end part of the first internal tube and the second internal tube includes a gas permeable film impermeable to each liquid, and permeable to the gas.

20 Claims, 21 Drawing Sheets

(56) References Cited

U.S. PATENT DOCUMENTS

| | | | |
|---|---|---|---|
| 2003/0199816 A1* | 10/2003 | Ramming | 604/89 |
| 2005/0101920 A1* | 5/2005 | Keane et al. | 604/218 |
| 2007/0020389 A1* | 1/2007 | Miyazawa | 427/248.1 |
| 2007/0020754 A1* | 1/2007 | Yuge et al. | 435/325 |
| 2007/0073267 A1* | 3/2007 | Muller | 604/506 |
| 2007/0123877 A1* | 5/2007 | Goldin et al. | 606/62 |
| 2007/0272763 A1* | 11/2007 | Dunne et al. | 239/8 |
| 2009/0240208 A1* | 9/2009 | Cowan | 604/190 |

FOREIGN PATENT DOCUMENTS

| | | | |
|---|---|---|---|
| JP | 07-100209 A | 4/1995 | |
| JP | 09-296039 A | 11/1997 | |
| JP | 11-502464 A | 3/1999 | |
| JP | 2001-57979 A | 3/2001 | |
| JP | 2001-515401 A | 9/2001 | |
| JP | 2002-282368 A | 10/2002 | |
| JP | 2005-152790 A | 6/2005 | |
| WO | WO 91/03224 A1 | 3/1991 | |
| WO | WO 95/31138 A1 | 11/1995 | |
| WO | WO 2007050971 A1 * | 5/2007 | |

OTHER PUBLICATIONS

U.S. Appl. No. 12/068,533, filed Feb. 7, 2008, Yokoyama, et al.
U.S. Appl. No. 12/199,880, filed Aug. 28, 2008, Yokoyama.
U.S. Appl. No. 12/120,041, filed May 13, 2008, Yatabe, et al.

\* cited by examiner

SPRAYER

TECHNOLOGICAL FIELD

The present invention generally relates to a device for delivering a liquid material. More specifically, the invention pertains to a sprayer having useful application in the medical field for spraying a liquid at a body region.

BACKGROUND DISCUSSION

Conventionally, there is known a method in which two or more liquids are mixed and ejected to an affected part or the like of a living body to form, for example, an anti-adhesive material, a biological tissue adhesive, etc. Thus, developmental efforts in the area of sprayers have been made.

Such a sprayer is configured to feed components which coagulate upon mixing, such as a thrombin-containing solution and a fibrinogen-containing solution, in a mutually separated manner to the vicinity of the affected part, and to spray them while mixing at the affected part. One conventional sprayer includes two syringes respectively containing different types of liquids, and a nozzle for mixing the liquids from respective syringes, and spraying the mixture. An example of this is disclosed in Japanese Application Publication No. 2002-282368. The sprayer described in this application publication is configured as follows: the nozzle is connected to a gas supply source for supplying an aseptic gas, so that the liquids are sprayed together with the aseptic gas. The nozzle is specifically configured in a double tube structure including two internal tubes through which the liquids from respective syringes pass, respectively, and an external tube in which the two internal tubes are positioned, and which passes the gas between it and the internal tubes. Then, in the respective inner tubes, the distal end openings respectively function as liquid ejection ports for respectively ejecting the liquids. Whereas, in the external tube, the distal end opening includes the liquid ejection ports disposed in the inside thereof, and functions as a gas ejection port for ejecting a gas.

With the nozzle thus configured, upon stopping the liquid ejection operation, the residual pressures in the respective internal tubes cause the liquids to project outward from the liquid ejection ports in the respective internal tubes. In this state, the liquids are mixed with each other so that the liquids coagulate. As a result, clogging occurs in each of the liquid ejection port. Further, the liquids ejected outward from the liquid ejection ports of the respective internal tubes also respectively extend to the gas ejection port. Accordingly, the liquids are also mixed with each other to coagulate at the gas ejection port, resulting in clogging. Then, when attempts are made to spray again with the sprayer in which clogging has occurred, the coagulated liquids inhibit the ejection of the liquids from respective liquid ejection ports, and the ejection of the gas from the gas ejection port. Thus, it is difficult to perform respray.

SUMMARY

A sprayer includes a syringe comprising a liquid-containing syringe barrel and a plunger movably positioned in the syringe barrel, a main body comprised of at least one syringe receiving area for receiving the syringe, a user operable operation part operable by the user to move the plunger within the syringe barrel when the syringe is positioned in the syringe receiving area to discharge the liquid from the syringe; and a nozzle comprising a liquid supply passage possessing an interior along which flows the liquid discharged from the syringe barrel, a gas supply passage connectable to a gas source and possessing an interior along which flows gas from the gas source, and a film separating the interior of the liquid supply passage and the interior of the gas supply passage. The film includes a plurality of through holes communicating the interior of the gas supply passage to the interior of the liquid supply passage so that gas in the interior of the gas supply passage flows through the through holes in the film and into the interior of the liquid supply passage.

According to another aspect, a sprayer comprises a nozzle comprised of a liquid flow path through which a liquid passes, and a gas flow path through which a gas for ejecting the liquid passes, and liquid supply means communicating with the liquid flow path for supplying the liquid to the liquid flow path, wherein the liquid flow path includes a gas permeable film, impermeable to the liquid and permeable to the gas, in at least a part of the wall part defining the liquid flow path.

In accordance with the sprayer disclosed here, when a liquid is ejected from the nozzle, gas permeates (flows into) the liquid flow path through a gas permeable film from a gas flow path, and the liquid ejects together with the gas. Then, when the ejection of the liquid is stopped, the residual pressure in the gas flow path causes the gas to flow into the liquid flow path through the gas permeable film. As a result, it is possible to blow off the liquid in the liquid flow path to the outside. This can help prevent the occurrence of clogging in the nozzle with reliability. Further, the gas ejects outwardly from the inside of the liquid flow path together with the liquid. The liquid can be in the form of an anti-adhesive material applied to a portion of a living body or a living tissue adhesive applied to as portion of a living body.

According to another aspect, a method of applying a liquid to a living body part comprises conveying the liquid along a liquid flow path, conveying a gas along a gas flow path, passing the gas through a gas permeable film possessing a plurality of through pores so that the gas in the gas flow path flows through the through pores and atomizes the liquid, and applying the atomized liquid to the living body part.

DETAILED DESCRIPTION

Figure 27:
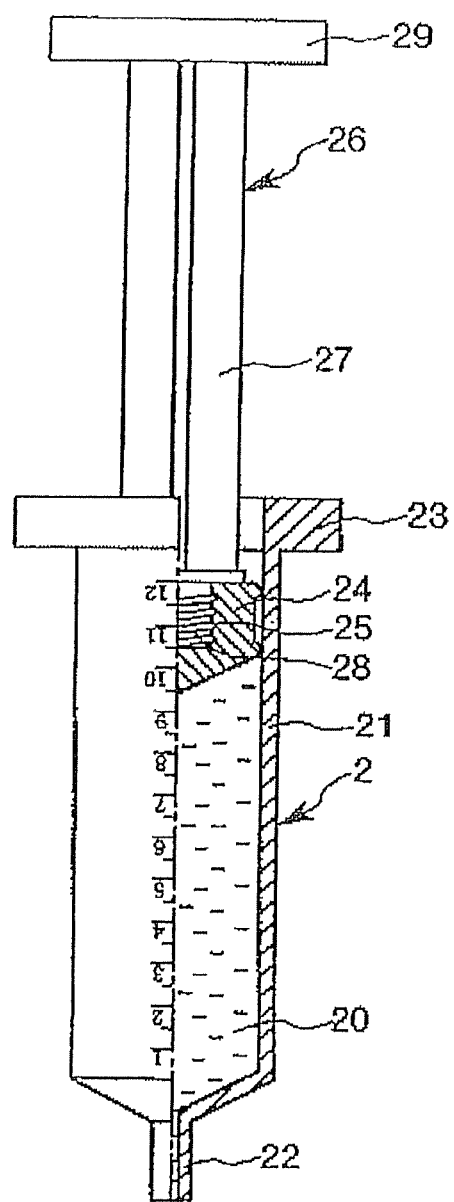
FIG. 27 is a partial longitudinal cross-sectional view of a first syringe to be mounted in the sprayer shown in FIG. 1.

FIGS. 1-9 illustrate aspects of a sprayer according to a first embodiment. For convenience in description, the left hand side in FIGS. 1, 2 and 5-9 is referred to as the distal end; and the right hand side is referred to as the rear end (proximal end). In FIG. 27, the lower side is referred to as the distal end, and the upper side is referred to as the rear end. Further, in FIGS. 1-4, the upper side is referred to as the top while the lower side is referred to as the bottom.

Figure 1:
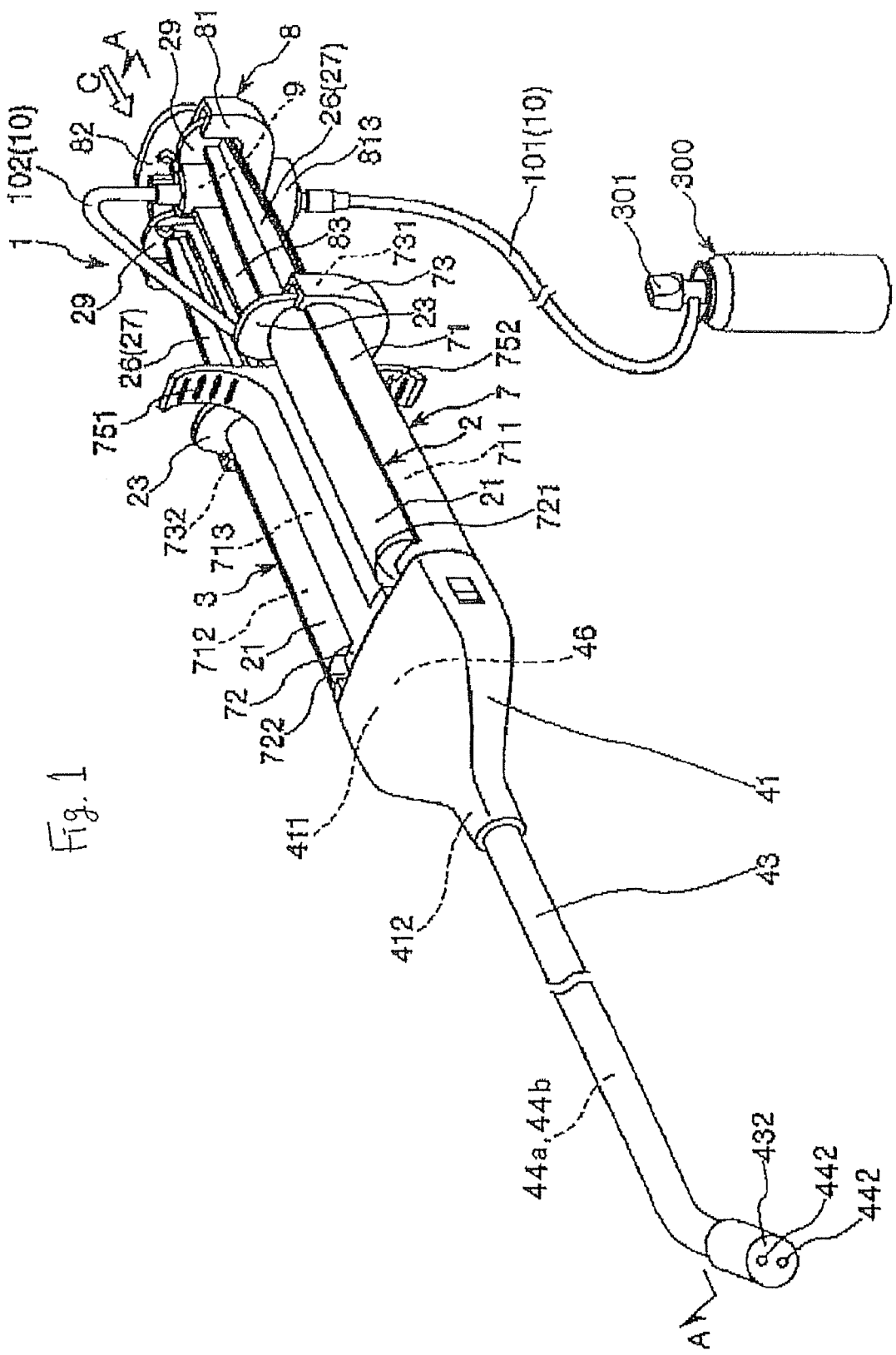
FIG. 1 is a perspective view of a sprayer according to a first embodiment disclosed herein.
Figure 2:
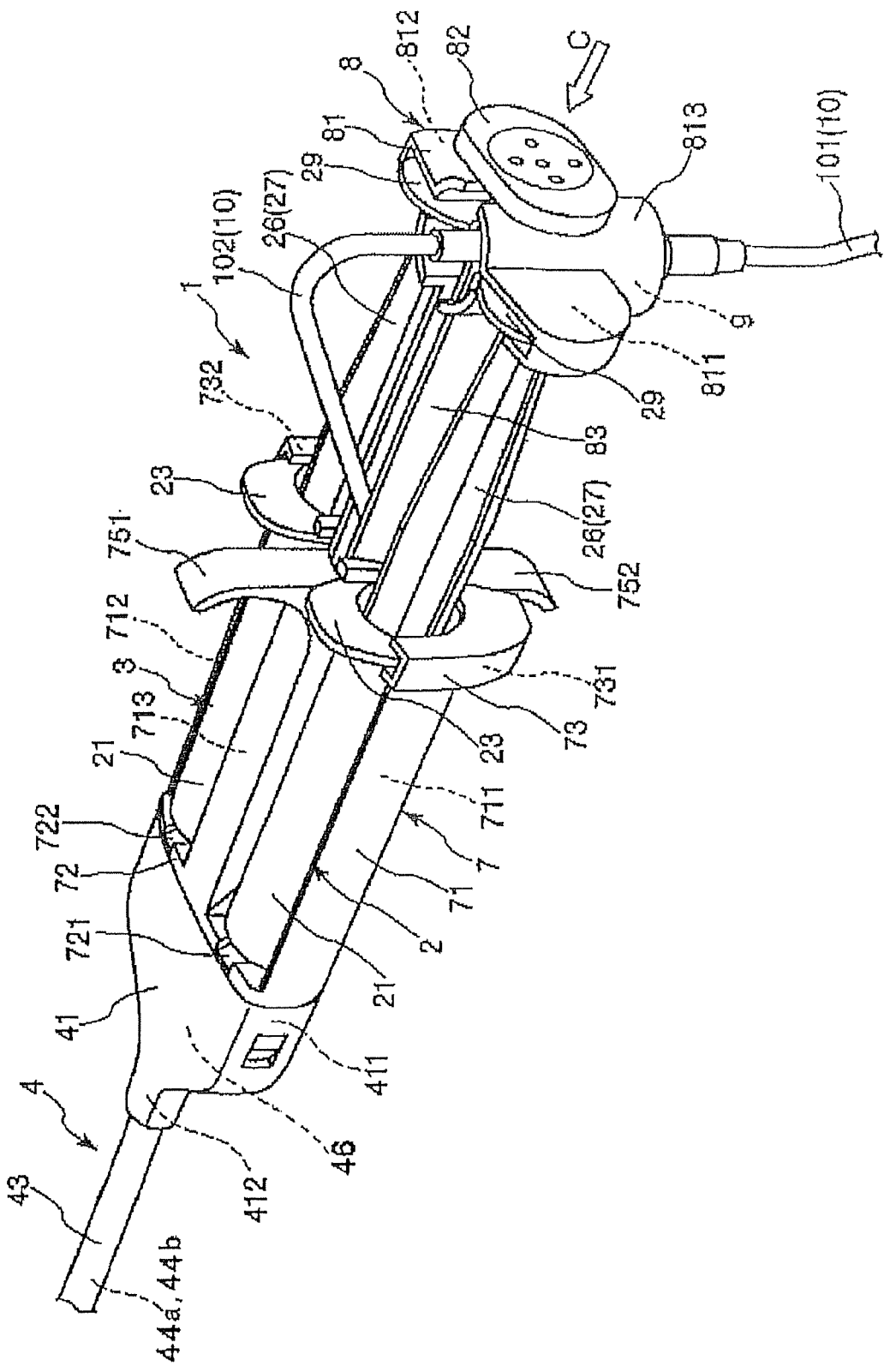
FIG. 2 is a perspective view of the sprayer shown in FIG. 1.
Figure 7:
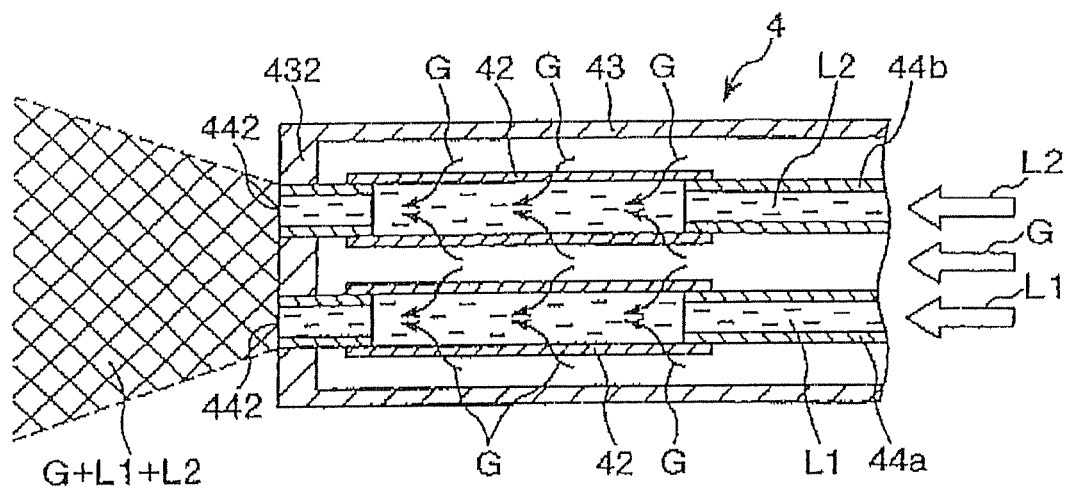
FIG. 7 is a fragmentary longitudinal cross-sectional view of the nozzle of the sprayer shown in FIG. 1, illustrating parts of the sprayer in another operational state.

The sprayer 1 disclosed here is configured to spray two types of liquids that are different in liquid composition from each other (a first liquid L1 and a second liquid L2), with the liquids being mixed during the spraying as generally illustrated in FIG. 7. As shown in FIGS. 1 and 2, the sprayer 1 is used with a first liquid-containing tube 2 (first syringe), forming a liquid supply means, and a second liquid-containing tube 3 (second syringe) forming a liquid supply means. Referring to FIG. 27, the first syringe 2 is filled with the first liquid L1 in a space 20 surrounded by an external tube or syringe barrel 21 and bounded by a gasket 24 at the end of a plunger 26 before being mounted in the sprayer 1. The second syringe 3 has the same construction as the first syringe shown in FIG. 27, such that a space is filled with the second liquid L2. that is surrounded by an external tube and bounded by a gasket.

The first liquid L1 to be filled in the first syringe 2 and the second liquid L2 to be filled in the second syringe 3 are different in composition (components) from each other. The first liquid L1 and the second liquid L2 are appropriately selected according to the use of the sprayer 1, the intended purpose, the case, and the like. For example, when the sprayer is used for administration of a biological tissue adhesive, one of the first liquid L1 and the second liquid L2 can be a liquid containing thrombin, and the other can be a liquid containing fibrinogen. Alternatively, when they are used for administration of an anti-adhesive material, one of the first liquid L1 and the second liquid L2 can be a liquid containing carboxymethyl dextrin modified with a succinimidyl group, and the other can be a liquid containing disodium hydrogenphosphate.

The first liquid L1 and the second liquid L2 are altered (i.e., gelate) upon mixing. The gelation enables, for example, the mixture of the first liquid L1 and the second liquid L2 (which is hereinafter referred to as a "liquid mixture") to reliably remain at the biological tissue (objective site) on which it is sprayed. Therefore, the liquid mixture can exhibit a function as a biological tissue adhesive or an anti-adhesive material at the objective site with reliability.

Needless to say, the types and the combinations of the first liquid L1 and the second liquid L2 are not limited to the ones described above.

During use, the respective plungers 26 of the first syringe 2 and the second syringe 3 are pressed and operated (i.e., a force is applied). As a result, it is possible to supply the first liquid L1 into the first internal tube or first liquid supply passage or tube 44a of a nozzle 4 (described later), and the second liquid L2 into the second internal tube or second liquid supply passage or tube 44b of the nozzle, with relative ease and reliability. The pressing operation of each plunger 26 can be manually carried out by an operator of the sprayer 1. For this reason, the operator can carry out spraying of the liquid mixture at his (or her) own timing.

As shown in FIG. 1, the sprayer 1 in which the first syringe 2 filled with the first liquid L1 and the second syringe 3 filled with the second liquid L2 are mounted comprises a sprayer main body 7, the nozzle 4, an operation part 8, an opening and closing means (valve mechanism) 9, and a tube (gas flow path) 10 connected to a cylinder (gas supply means) 300. Before describing the respective parts forming the sprayer 1, the cylinder 300 will be described.

The cylinder 300 includes an internal space containing (filled with) a high pressure (compressed) gas G. Thus, the cylinder 300 can supply the gas G to the sprayer 1 (nozzle 4). The cylinder 300, is provided with a closable valve (cock) 301 for controlling the supply of the gas G with respect to the sprayer 1. For example, the closable valve 301 permits the gas G to be supplied to the sprayer and prevents the gas G from being supplied to the sprayer 1. When the sprayer 1 is used, the valve 301 is positioned in an open state.

The gas G is not restricted to any particular gas. An example of a suitable gas is carbon dioxide. The gas G is preferably in an aseptic state. However, it doesn't matter whether the gas G is in an aseptic state, or not. The internal pressure (gas pressure) in the cylinder 300 is preferably 0.01 MPa or more, more preferably 0.05 to 1 MPa.

As shown in FIGS. 1 and 2, the sprayer main body 7 is configured to fix the first syringe 2 and the second syringe 3 side by side, in parallel relation to one another. The sprayer main body 7 includes a base 71, a front plate (first fitting part) 72 at the distal end of the base 71, a rear plate (second fitting part) 73 at the rear end of the base 71, and finger rest parts 751, 752 in the vicinity of the rear plate 73 of the base 71. The upper part of the base 71 includes concave parts 711, 712 that are parallel to one another and roughly shaped in a semi-circular arc in cross section. The external tube 21 of the first syringe 2 is stored in the concave part 711. The external tube 21 of the second syringe 3 is stored in the concave part 712.

The front plate 72 is positioned at the distal end of the base 71. Grooves 721, 722 are formed in the front plate 72 at the positions respectively corresponding to the concave parts 711, 712. When the first syringe 2 and the second syringe 3 are mounted, the reduced diameter part 22 of the first syringe 2 is inserted into the groove 721, and the reduced diameter part 22 of the second syringe 3 is inserted into the groove 722.

The rear plate 73 is provided at the rear end of the base 71. In the rear plate 73, the concave parts 731, 732 are formed at positions respectively corresponding to the concave parts 711, 712. When the first syringe 2 and the second syringe 3 are mounted, the flange 23 (the proximal end part) of the first syringe 2 is fitted (inserted) into the concave part 731, and the flange 23 (proximal end part) of the second syringe 3 is fitted into the concave part 732.

Thus, in the sprayer main body 7, each reduced diameter part 22 is fitted into the front plate 72, and each flange 23 is fitted into the rear plate 73. As a result, it is possible to fix the first syringe 2 and the second syringe 3 at positions parallel to one another.

The finger rest parts 751, 752 are provided in the vicinity of the rear plate 73 of the base 71. The user's fingers can rest on the finger rest parts 751, 752 for use of the sprayer 1. The finger rest part 751 is configured as an upwardly protruding plate piece, and the finger rest part 752 is configured as a downwardly protruding plate piece. Further, respective finger rest parts 751, 752 are configured such that the sides facing the distal end direction each form a circular arc (curved concave shape).

The sprayer main body 7 may be configured such that respective parts forming the sprayer main body 7 are integrally formed, or may be configured such that respective parts are respectively formed of separate bodies, with these bodies being bonded together.

The material forming the sprayer main body 7 is not limited to a particular material. Examples of materials that can be used include various metal materials, various plastics, and the like used alone, or in combination thereof.

On the rear end side of the sprayer main body 7, the operation part 8 is set movably in the longitudinal direction with respect to the sprayer main body 7. The operation part 8 is a site for pressing and operating the plunger 26 of the first syringe 2 and the plunger 26 of the second syringe 3 in the distal end direction (in the direction of the arrow C in FIGS. 1, 2, and 4). The operation part 8 has a connection part 81 for connecting the flanges 29 of the plungers 26 of the first syringe 2 and the second syringe 3, a pressing part 82 situated on the rear end side of the connection part 81, and a rail part 83 extending from the connection part 81 in the distal end direction.

Upwardly opening concave parts 811, 812 are provided in the connection part 81. The concave part 811 possesses a shape corresponding to the flange 29 of the plunger 26 of the first syringe 2, in which the flange 29 is fitted (see FIG. 2). Whereas, the concave part 812 possesses a shape corresponding to the flange 29 of the plunger 26 of the second syringe 3, in which the flange 29 is fitted (see FIG. 2). With the connection part 81 configured in this manner, it is possible to connect and fix the flanges 29 of the plungers 26 of the first syringe 2 and the second syringe 3. As a result, it is possible to move these plungers 26 integrally (together at the same time) in the direction of the arrow C.

In the connection part 81, a tubular part 813 formed as a tube is provided between the concave part 811 and the concave part 812. The tubular part 813 is positioned so that its axis is parallel with the vertical direction in FIG. 1 (the same also applies to FIG. 2). Further, most of the opening and closing means 9 is stored in the tubular part 813.

At the outer circumferential part of the tubular part 813 of the connection part 81, a long-shaped rail part 83 is formed in a manner protruding in the distal end direction. The rail part 83 is provided at the base 71 of the sprayer main body 7, and is inserted into a long-shaped guide 713. The pressing operation in the direction of the arrow C of the operation part 8 guides the rail part 83 to the guide 713. As a result, it is possible to carry out the pressing operation relatively smoothly.

The plate-shaped pressing part 82 is set movably, in the longitudinal direction of the sprayer main body 7, on the rear end side of the tubular part 813 of the connection part 81.

The pressing part 82 is a site pressed by a user when the sprayer 1 is used, i.e., the mixture is sprayed onto the affected part or the like. When the sprayer 1 is used, an index finger, for example, can be rested on the finger rest part 751, a middle finger can be rested on the finger rest part 752, and a thumb can be rested on the pressing part 82. As a result, it is possible to grasp the sprayer 1 with relative stability and reliability. Further, it is possible to carry out the pressing operation of the operation part 8 (pressing part 82) relatively smoothly. This results in an improvement of the operability of the sprayer 1.

The pressing part 82 is connected to a second connection part 92 of the opening and closing means 9 described later.

The material forming the operation part 8 is not limited to a particular material. Examples of suitable materials include those mentioned above as examples of materials for the sprayer main body 7.

As described above, in the tubular part 813 of the operation part 8, the opening and closing means 9 is set. The opening and closing means 9 is for shutting off/permitting the flow of the gas G from the cylinder 300 to the nozzle 4. The first tube 101 and the second tube 102 are shut off (see FIG. 3)/communicate with each other (see FIG. 4) through the opening and closing means 9, i.e., by the operation of the opening and closing means 9.

Figure 3:
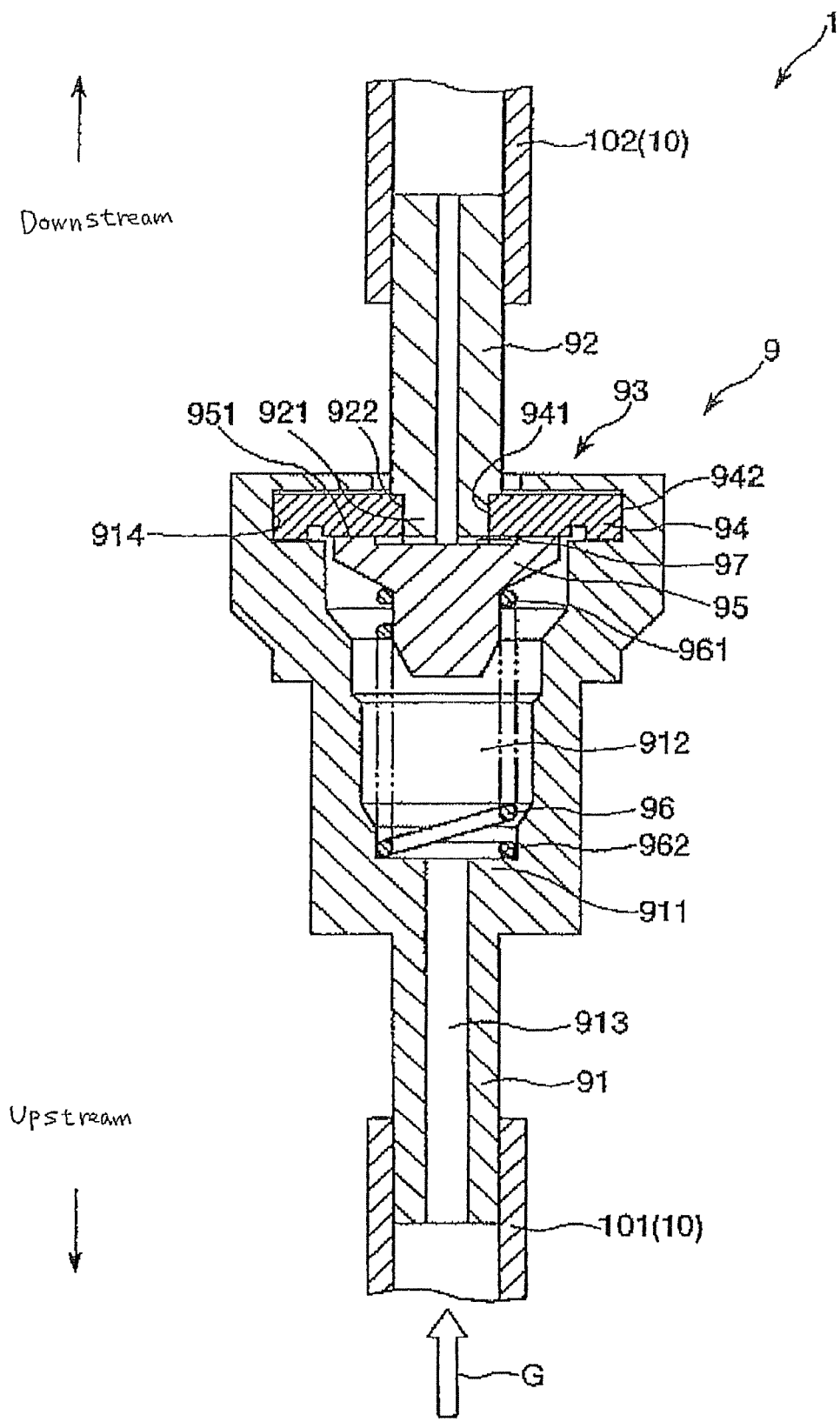
FIG. 3 is a cross-sectional view of the sprayer taken along the section line A-A in FIG. 1 illustrating the opening/closing means of the sprayer (in the closed state of the gas passage).
Figure 4:
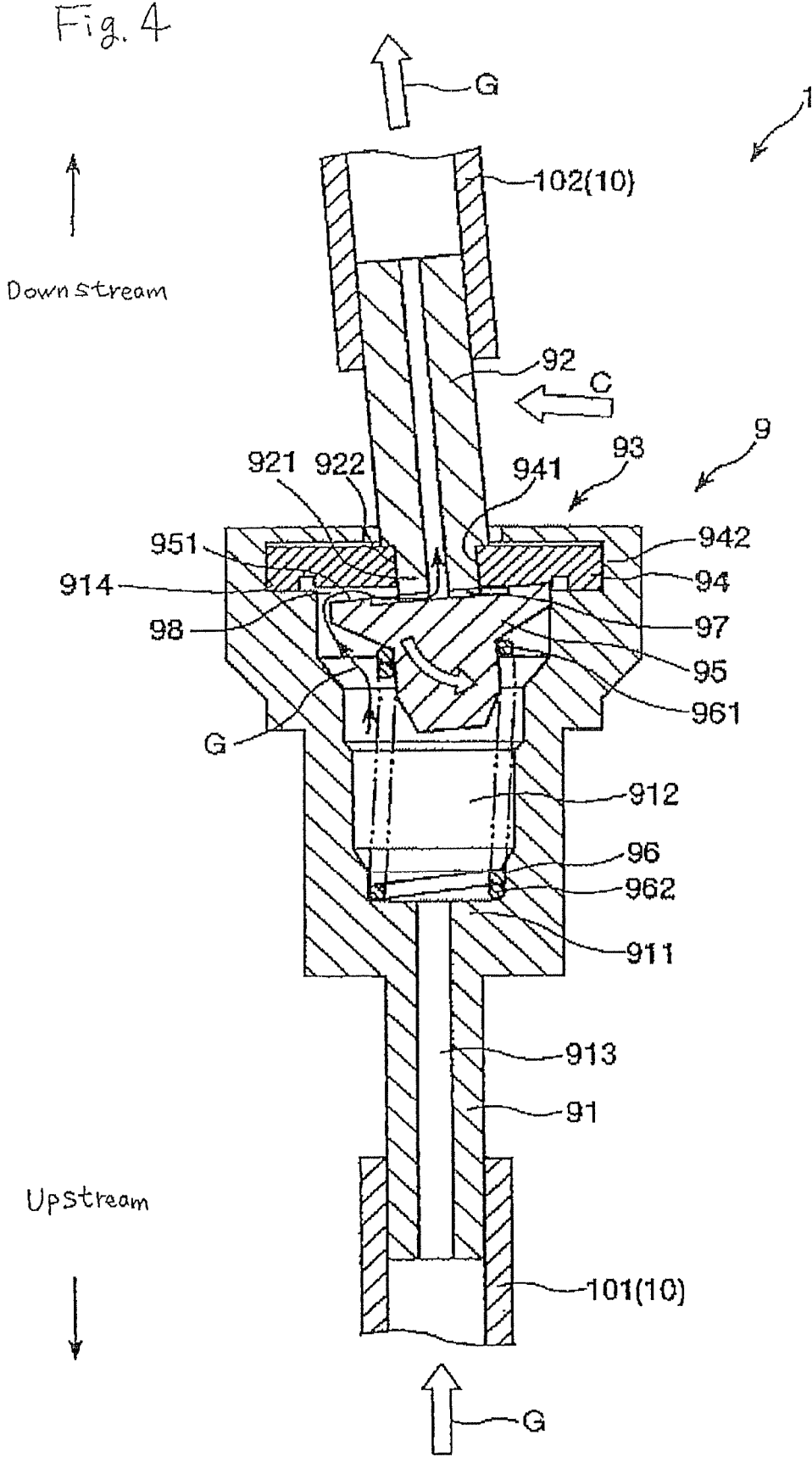
FIG. 4 is a cross-sectional view of the sprayer taken along the section line A-A in FIG. 1 illustrating the opening/closing means of the sprayer (in the opened state of the gas passage).

As shown in FIGS. 3 and 4, the opening and closing means 9 has a first connection part 91 connected to the first tube 101, a second connection part 92 connected to the second tube 102, and a closable valve part 93 stored in the first connection part 91.

The first connection part 91 is in the shape of a tube. The bore of the first connection part 91 is provided with a storage part 912 situated on the downstream side and in which the valve part 93 is stored. Further, the bore of the first connection part 91 is provided with a reduced diameter bore part 913 reduced in diameter relative to the inner diameter on the upstream side of the storage part 93. A step 911 is formed at the boundary between the reduced diameter part 913 and the storage part 912. The step part 911 exhibits a sharp change in inner diameter.

The second connection part 92 is in the shape of a tube. As described above, the second connection part 92 is connected to the pressing part 82 of the operation part 8. The second connection part 92 is supported at a bottom part 921 by a sealing member 94 of the valve part 93. Thus, it is set on the downstream side of the first connection part 91 via the sealing member 94. The second connection part 92 is displaceably positionable in a first posture in which its axis is the same as (coaxial with) the axis of the first connection part 91 (the state shown in FIG. 3) and in a second posture in which the axis of the second connection part 92 is tilted (relative to the axis of the first connection part 92) in the direction of the arrow C (direction of operation) of the pressing part 82 (operation part 8) with the bottom part 921 as the fulcrum (the state shown in FIG. 4).

The valve part 93 comprises the sealing member 94 formed of an elastic material, a flange part 95 situated on the upstream side of the sealing member 94, and an urging part 96 for urging the flange part 95 to the side of the sealing member 94.

The sealing member 94 is in the shape of a ring. The sealing member 94 is in close contact with an outer circumferential part 922 of the bottom part 921 of the second connection part 92 at its inner circumferential part 941. An outer circumferential part 942 of the sealing member 94 is in close contact with an inner circumferential part 914 of the storage part 912 of the first connection part 91. With such a sealing member 94, the first connection part 91 and the second connection part 92 are air-tightly connected via the sealing member 94.

The flange part 95 has an outer diameter larger than the outer diameter of the second connection part 92. The flange part 95 is disposed in an opposing relation with the bottom side of the second connection part 92 via a gap 97.

The urging part 96 is in the form of a compressed coil spring in this embodiment. It is, in a compressed state, in contact with the flange part 95 at its upper edge 961, and in contact with the step part 911 of the first connection part at its bottom part 962. This can urge the flange part 95 to the side of the sealing member 94.

With the valve part 93 having such a configuration, when the second connection part 92 is in the first posture, i.e., when an external force is not applied to the second connection part 92, the flange part 95 is urged onto the urging part 96 to be air-tightly brought into close contact with the sealing member 94 (see FIG. 3). As a result, the valve part 93 is rendered in a closed state.

Referring to FIG. 4, when a pressing force in the direction of the arrow C by the pressing part 82 of the operation unit 8 acts on the second connection part 92, the second connection part 92 is displaced from the first posture to the second posture. At this step, the flange part 95 is displaced against the urging force of the urging part 96. As a result, a part (or the whole) of a peripheral part 951 of the flange part 95 is separated apart from the sealing member 94. This results in the formation of a gap 98 between it and the sealing member 94 as shown in FIG. 4. As a result, the gas G flows from the first connection part 91 into the second connection part 92 via the gap 98. Thus, the valve part 93 is positioned in an opened state.

With the opening and closing means 9 having the foregoing configuration, the valve part 93 can be opened/closed in synchronization with the pressing operation by the operation part 8. As a result, when the valve part 93 is in a closed state, the flow of the gas G from the cylinder 300 to the nozzle 4 can be shut off with reliability. When the valve part 93 is in an opened state, the flow of the gas G is opened or permitted.

The materials forming the first connection part 91, the second connection part 92, the flange part 95, and the urging part 96 are not particularly limited. However, for example, various metal materials and various plastics may be used alone or in combination thereof.

The materials forming the sealing member 94 are also not necessarily limited. However, by way of example, various rubber materials such as natural rubber, butyl rubber, isoprene rubber, butadiene rubber, styrene-butadiene rubber, and silicone rubber can be used. As shown in FIGS. 1 and 2, the front plate 72 of the sprayer main body 7 includes a nozzle 4 set therein. The nozzle 4 ejects the gas G (gas) which has passed through the tube 10, the first liquid L1 which has passed through the reduced diameter part 22 of the first syringe 2, and the second liquid L2 which has passed through the reduced diameter part 22 of the second syringe 3.

The fixing member 44 is formed of, for example, a metal material or a resin material, and has an outer shape of a block. The fixing member 41 has a hollow part opening at the distal end and the proximal end thereof. With such a fixing member 41, the proximal end opening 411 is fitted to the front plate 72 of the sprayer main body 7. As a result, the nozzle 4 is fixed to the sprayer main body 7.

The nozzle 4 has a first internal tube 44a (liquid flow path), which is connected to the reduced diameter part 22 of the first syringe 2, and through which the first liquid L1 passes, a second internal tube 44b (liquid flow path), which is connected to the reduced diameter part 22 of the second syringe 3, and through which the second liquid L2 passes, an external tube 43 into which the first internal tube 44a and the second internal tube 44b are inserted, a supply tube (gas supply tube) 46 connected to a second tube 102 for supplying the gas G in the external tube 43, and the fixing member 41 for fixing the nozzle 4 to the front plate 72 of the sprayer main body 7.

The first internal tube 44a, the second internal tube 44b, the external tube 43, and the supply tube 46 may each be either formed of a hard material, or formed of a soft material, an elastic material, or the like, and having flexibility. In this embodiment, each of the noted tubes is constructed to possess flexibility. Examples of the constituent material may include: polyvinyl chloride, polyethylene, polypropylene, styrene-butadiene rubber, silicone rubber, various thermoplastic elastomers of a polyurethane type, a polyester type, a polyamide type, an olefin type, a styrene type, and the like, stainless steel, and aluminum or the like. The first internal tube 44a and the second internal tube 44b have roughly the same configuration. Therefore, the first internal tube 44a will be described, it being understood that the same applies to the second internal tube 44b.

The first internal tube 44a is formed of a long-shaped tube-like body. The proximal end part thereof is connected to the reduced diameter part 22 of the first syringe 2.

The first internal tube 44a has an ejection port 442 opening at the distal end. The ejection port 442 is a site for ejecting the fist liquid L1 flowing from the reduced diameter part 22 of the first syringe 2 upon pressing and operating the operation part 8, and the gas G flowing from the cylinder 300.

Such a first internal tube 44a and second internal tube 44b are positioned in the external tube 43 as seen in FIGS. 5-9. The external tube 43 is formed of a long-shaped tube-like body. The proximal end part of the external tube 43 is connected to the distal end opening 412 of the fixing member 41. The gas G supplied via the supply tube 46 passes through (the gap (gas flow path)) between the external tube 43 and the first internal tube 44a and the second internal tube 44b.

The external tube 43 has a distal end wall part 432 provided at the distal end part, so that the distal end is closed. The first internal tube 44a and the second internal tube 44b penetrate through the distal end wall part 432, so that respective ejection ports 442 are exposed. Between the distal end wall part 432 of the external tube 43 and the distal end parts of the first internal tube 44a and the second internal tube 44b, for example, a sealing member is set, so that the air tightness in the external tube 43 is kept. As a result, the gas G is prevented from leaking from between the distal end wall part 432 of the external tube 43 and the distal end parts of the first internal tube 44a and the second internal tube 44b. As shown in FIGS. 1 and 2, the fixing member 41 is disposed at the proximal end part of the nozzle 4. The fixing member 41 includes a hollow body having a distal end opening 412 and the proximal end opening 411. To the distal end opening 412, the proximal end part of the external tube 43 is air-tightly connected. The proximal end opening 411 is connected/fixed to the front plate 72 of the sprayer main body 7. Whereas, in the inside of the fixing member 41, the connection part of the first internal tube 44a to the first syringe 2, the connection part of the second internal tube 44b to the second syringe 3, and the connection part of the supply tube 46 to the tube 10 are positioned. As a result, respective connection parts can be covered, so that respective connection parts can be protected.

As shown in FIGS. 5-9, at least the distal end part (the portion in the vicinity of the ejection port 422) of the wall part of the first internal tube 44a is formed of a gas permeable film 42. Similarly, the wall part of the second internal tube 44b is formed of a gas permeable film 42 at least at the distal end part (the portion in the vicinity of the ejection port 422). Both of the gas permeable films 42 have the same configuration. Therefore, the description below of the gas permeable film 42 on the first internal tube 44a side applies equally to the gas permeable film on the second internal tube 4b side.

The gas permeable film 42 allows the gas G in the external tube 43 to permeate therethrough, but does not permit liquid such as the liquid L1 (L2) to permeate therethrough. As a result, the gas G can flow into the first internal tube 44a through the gas permeable film 42, yet the liquid L1 (L2) in the first internal tube 44a does not flow outwardly through the gas permeable film 42. Accordingly, the flowing gas G is ejected from the ejection port 442 together with the first liquid L1 as schematically illustrated in FIG. 7. As a result, the first liquid L1 is atomized, and mixed with the second liquid L2 which has similarly been ejected in an atomized form, to be sprayed onto the affected part.

The gas permeable film 42 can be configured to span the distance between cut parts of the first internal tube 44a. That is, the first internal tube 44a can be cut at two spaced apart locations, and the portion of the first internal tube 44a between the two cuts removed. The gas permeable film 42 is then fixed to the two spaced apart parts of the first internal tube 44a. That is, the gas permeable film 42 is fixed or bonded to the portion on the upstream side (proximal end side) and the downstream side (distal end side) of the first internal tube 44a. The bonding method is not particularly restricted and can take various forms. Examples may include the methods of fusion (heat fusion, high frequency fusion, ultrasonic fusion, and the like), and adhesion (adhesion by an adhesive or a solvent).

Figure 5:
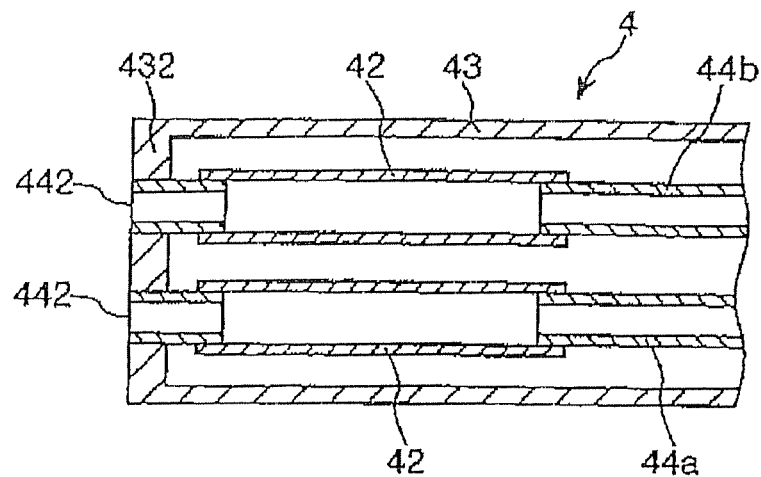
FIG. 5 is a fragmentary longitudinal cross-sectional view of the nozzle of the sprayer shown in FIG. 1, illustrating parts of the sprayer in one operational state.
Figure 8:
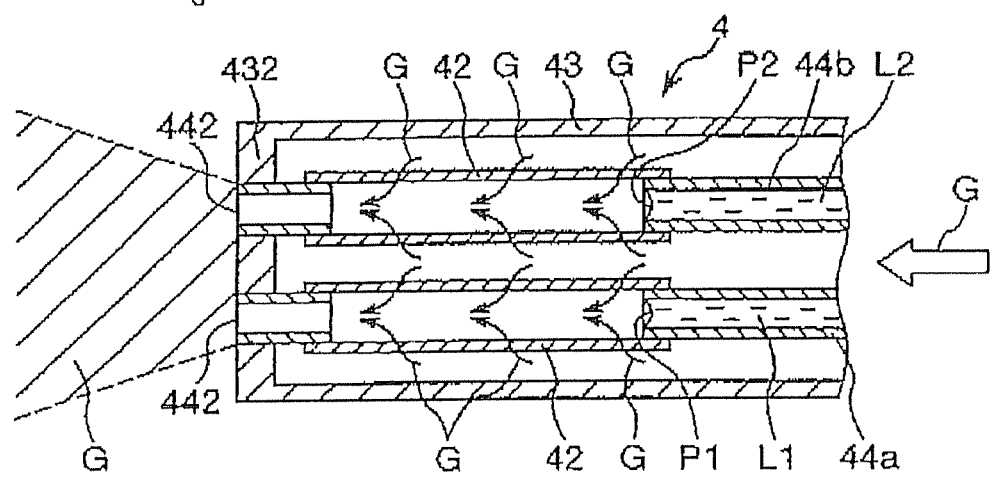
FIG. 8 is a fragmentary longitudinal cross-sectional view of the nozzle of the sprayer shown in FIG. 1, illustrating parts of the sprayer in another operational state.
Figure 9:
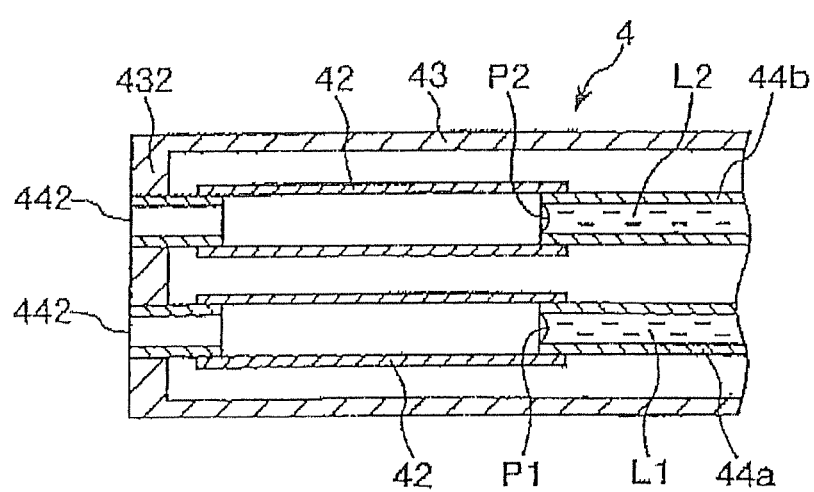
FIG. 9 is a fragmentary longitudinal cross-sectional view of the nozzle of the sprayer shown in FIG. 1, illustrating parts of the sprayer in another operational state.

As shown in FIG. 5 (the same also applies to FIGS. 6-9), the gas permeable film 42 has an overall shape of a tube. This enables the gas G to flow into the first internal tube 44a from any portion of the surrounding circumferential extent via the gas permeable film 42. As a result, it is possible to supply the gas G into the first internal tube 44a in a manner that is neither too much nor too little. Accordingly, the first liquid L1 ejected from the ejection port 442 is rendered in an atomized form. By thus having been rendered in an atomized form, the first liquid L1 and the second liquid L2 are relatively uniformly mixed, and sprayed in a preferred state (uniformly mixed state) to the affected part. Whereas, as shown in FIG. 8, when ejection of the first liquid L1 is stopped, the gas G which has passed through the gas permeable film 42 outwardly blows the first liquid L1 in the first internal tube 44a at the portion closer to the distal end than the gas permeable film 42. This helps prevent the first liquid L1 from remaining at the ejection port 422. As a result, clogging is inhibited or prevented from occurring in the ejection port 442 (nozzle 4) as generally illustrated in FIG. 9.

The gas permeable film 42 which allows the gas G to permeate therethrough includes a large number of pores. The pores penetrate the gas permeable film 42 in the thickness direction of the gas permeable film 42. The average pore diameter of these pores is not particularly limited. However, an example of a preferable diameter is 2 µm or less. An example of a gas permeable film which can be used to form the gas permeable film 42 having such pores may include "POREFLON TUBE (TB-0201)" manufactured by Sumitomo Electronic Fine Polymer, Inc. This is a gas permeable film 42 having an average pore diameter of about 1 µm.

Setting the pore diameter at 0.01 to 0.45 µm allows the gas G to permeate through the gas permeable film 42, and the gas permeable film 42 has a germ impermeability. As a result, even if the gas G in the cylinder 300 is not in an aseptic condition, germs in the gas G are removed by the gas permeable film 42, and inhibited or prevented from flowing into the first internal tube 44a. This helps enable the first liquid L1 (liquid mixture) in an aseptic condition to be sprayed to the affected part.

The film thickness (wall thickness) of the gas permeable film 42 is not limited to a particular thickness. For example, the film thickness is preferably 0.1 to 1 mm, and more preferably 0.3 to 0.8 mm.

The surface area (area of the external circumferential surface) of the gas permeable film 42 is preferably 20 to 200 mm$^2$, and more preferably 40 to 100 mm$^2$.

As generally mentioned above, the gas permeable film 42 also possesses an impermeability (water repellency), namely, a hydrophobicity against the first liquid L2 and the second liquid L2. As a result, the first liquid L1 in the first internal tube 44a is prevented from flowing back (flowing) into the external tube 43 via the gas permeable film 42. Such a gas permeable film 42 is one formed of a material having hydrophobicity, or the one the surface of which is subjected to a hydrophobization processing. Examples of the material (constituent material) having hydrophobicity may include: polytetrafluoroethylene (PTFE), a copolymer of tetrafluoroethylene and hexafluoropropylene (FEP), a copolymer of tetrafluoroethylene and perfluoroalkyl vinyl ether (PFA), polychlorotrifluoroethylene (PCTFE), polyvinylidene fluoride (PVDF), a copolymer of ethylene and tetrafluoroethylene (ETFE), a copolymer of ethylene and chlorotrifluoroethylene (ECTFE), and polypropylene (PP). Preferably used gas permeable films 42 are obtained by making these materials porous with a method such as a drawing method, a microphase separation method, an electron beam etching method, a sintering method, or a method of argon plasma particles, or the like. The hydrophobization processing is not particularly limited. Examples of such processing may include a method in which the material having hydrophobicity is coated on the surface of the gas permeable film 42.

In this embodiment, the gas permeable film 42 forms the distal end portion of the wall part of the first internal tube 44*a*, but gas permeable film is not limited in that regard. For example, the gas permeable film 42 may form the entirety of the wall part of the first internal tube 44*a*. Alternatively, it is sufficient only that a part of the circumferential extent of the first internal tube 44*a* is formed by the gas permeable film 42.

Set forth below is a description of the operation of the sprayer 1 in a usable state, i.e., including the first syringe 2 filled with the first liquid L1 and the second syringe 3 filled with the second liquid L2 mounted therein, and connected to the cylinder 300.

The first syringe 2 and the second syringe 3 are filled with the first liquid L1 and the second liquid L2 respectively, each in an amount necessary to be sprayed onto the affected part. With respect to the cylinder 300, the valve 301 is in an opened state, which allows the gas G to be supplied to the sprayer 1.

The sprayer 1 is configured so that the force for causing the gap 98 between the sealing member 94 and the flange part 95 against the force of the urging part 96 pressing the flange part 95 against the sealing member 94, i.e., the pressing force in the direction of the arrow C to tilt the second connection part 92 from the first posture to the second posture, is set to be smaller than the force to move the plunger 26 of the first syringe 2 and the plunger 26 of the second syringe 3 in the direction of the distal end. In other words, before moving the plungers 26, the gap 98 is created, and the gas G is supplied. Such setting can be done in the following manner. For example, various conditions such as the spring constant of the urging part 96, the viscosity of each liquid, and the inner diameter of each external tube 21 are appropriately set.

With such a sprayer 1, first an index finger is rested on the finger rest part 751 of the sprayer main body 7, a middle finger is rested on the finger rest part 752, and a thumb is rested on the pressing part 82 of the operation part 8. These references to the index finger, middle finger and thumb are examples. At this step, the first liquid L1 is not supplied to the first internal tube 44*a*, the second liquid L2 is not supplied to the second internal tube 44*b*, and the gas G is not also supplied to the external tube 43 (supply tube 46) (see FIG. 5). Accordingly, the gas G, the first liquid L1, and the second liquid L2 are not ejected from the nozzle 4.

Figure 6:
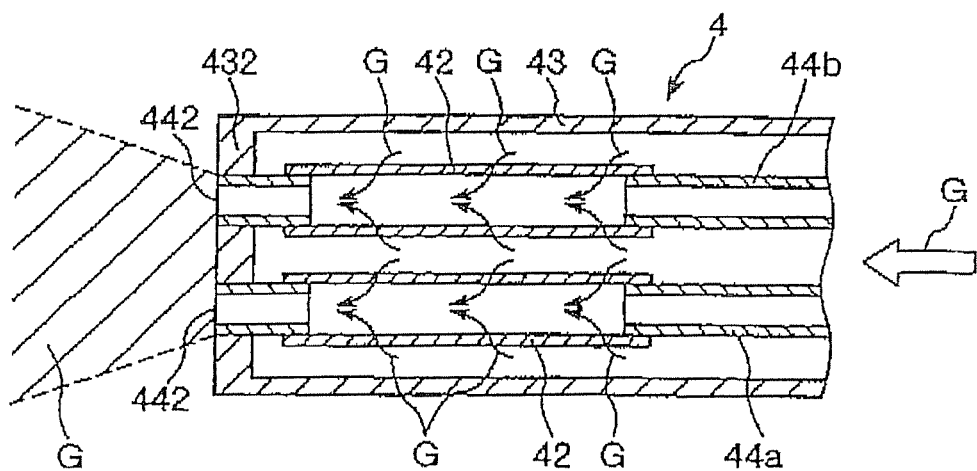
FIG. 6 is a fragmentary longitudinal cross-sectional view of the nozzle of the sprayer shown in FIG. 1, illustrating parts of the sprayer in another operational state.

Then, when the pressing part 82 is pressed and operated with a thumb in this state, the second connection part 92 is initially tilted. As a result, the gap 98 is created between the sealing member 94 and the flange part 95. Thus, the gas G passes through the gap 98 as illustrated in FIG. 4. As a result, the gas G flows into the supply tube 46 through the second tube 102, and thereby further passes through the inside of the external tube 43. Then, when the gas G reaches the vicinity of each gas permeable film 42, it flows into the first internal tube 44*a* and the second internal tube 44*b* through the gas permeable film 42. The gas G ejects at high speed from each ejection port 442 as illustrated in FIG. 6.

The pressing operation on the pressing part 82 by a thumb falls short of moving the whole operation part 8, namely each plunger 26 in the direction of the distal end. For this reason, the first liquid L1 and the second liquid L2 are not yet supplied to the first internal tube 44*a* and the second internal tube 44*b*, respectively.

The pressing part 82 is further pressed. Then, the second connection part 92 is tilted to the limit, so that the pressing force from the thumb is transferred to the connection part 81 via the pressing part 82. As a result, the connection part 81 (the whole operation part 8) starts to move. Accordingly, the first liquid L1 is pushed out from the first syringe 2, and the second liquid L2 is also pushed out from the second syringe 3. The pushed first liquid L1 merges or mixes with the gas G in the gas permeable film 42, and is ejected from the ejection port 442 of the first internal tube 44*a* together with the gas G as generally shown in FIG. 7. Whereas, roughly as with the first liquid L1, the second liquid L2 merges or mixes with the gas G in the gas permeable film 42, and is ejected from the ejection port 442 of the second internal tube 44*b* together with the gas G as shown in FIG. 7.

The first liquid L1 and second liquid L2 ejected from respective ejection ports 442 are respectively atomized by the gas G being ejected at high speed. As a result, the first liquid L1 and the second liquid L2 are mutually mixed to be sprayed onto the affected part.

After completion of spraying of the mixture in a prescribed amount onto the affected part, the pressing force against the pressing part 82 (operation part 8) by the thumb is eased or starts being released. Then, first, the movement of the whole operation part 8 is stopped. This stops the movement of each plunger 26, so that ejection of the first liquid L1 and the second liquid L2 is individually stopped as depicted generally in FIG. 8. At this point, the second posture of the second connection part 92 by pressing of the pressing part 82 is maintained, and hence the gas G is still ejected as shown in FIG. 8. Accordingly, in the first internal tube 44*a*, the first liquid L1 at the portion closer to the distal end than the gas permeable film 42 is pushed out of the ejection port 442 by the gas G which has flowed through the gas permeable film 42. As a result, the distal end P1 of the first liquid L1 is situated in the vicinity of the proximal end part of the gas permeable film 42. Also, in the second internal tube 44*b*, the second liquid L2 at the portion closer to the distal end than the gas permeable film 42 is pushed out of the ejection port 442 by the gas G which has flowed through the gas permeable film 42. As a result, the distal end P2 of the second liquid L2 is situated in the vicinity of the proximal end part of the gas permeable film 42.

With such a configuration, the first liquid L1 and the second liquid L2 are inhibited or prevented from remaining in the vicinity of their respective ejection ports 442. Further, these liquids are prevented from being mixed (coming in contact with each other), and gelating. This helps prevent clogging from occurring in each ejection port 442.

Further, when the pressing force against the pressing part 82 by the thumb is eased, the thumb which has pressed the pressing part 82 is finally separated from the pressing part 82. As a result, the pressing force against the second connection part 92 is released. Thus, the second connection part 92 returns to the first posture. As a result, the gap 98 between the sealing member 94 and the flange part 95 disappears. Namely, the sealing member 94 and the entire circumference of the peripheral part 951 of the flange part 95 come in close contact with each other as illustrated in FIG. 3. At this step, supply of the gas G to the supply tube 46 is stopped as depicted in FIG. 9. In this manner, upon completion of the operation with respect to the sprayer 1, namely, after use of the sprayer 1 (after spraying), clogging is inhibited or prevented from occurring in the nozzle 4. Then, the sprayer 1 with no clogging occurring therein can be used for spraying the affected part again.

The sprayer 1 is configured such that the gas G is ejected in advance of the first liquid L1 and the second liquid L2. This can help prevent only the first liquid L1 and the second liquid L2 from being ejected and sprayed onto the affected part. Further, the first liquid L1 and the second liquid L2 are respectively ejected in an atomized form by the gas G ejected in advance. As a result, these liquids are mixed with each other.

Further, even after the supply of the gas G (the state shown in FIG. 9) is stopped, the gas G flows into the first internal tube 44a via the gas permeable film 42 by the residual pressure in the external tube 43. Therefore, the first liquid L1 at the portion closer to the distal end than the gas permeable film 42 can be further blown away. This can help prevent clogging from occurring in each ejection port 442.

FIGS. 10-14 illustrate aspects of the nozzle and syringe in a sprayer according to a second embodiment. Features in this second embodiment that are the same as those in the first embodiment are designated by the same reference numeral, and a detailed description of such features is not repeated. The description below will primarily describe differences in this embodiment relative to the first embodiment described above.

This embodiment is the same as the first embodiment, except for further having a volume variation part and an expansion part for deforming it.

As shown in FIGS. 10-14, the sprayer 1A includes volume variation parts 441 deformable in such a manner as to vary the internal volume. The volume variation parts 441 are provided in the vicinity of the sprayer main body 7, midway along the first internal tube 44a and midway along the second internal tube 43b. The volume variation part 441 in the first internal tube 44a and the volume variation part 441 in the second internal tube 44b are disposed at symmetric positions with respect to the supply tube 46.

An expansion part (balloon) 461 which expands/shrinks (contracts) according to the flow rate (supply amount) of the gas G is provided midway along the supply tube 46. The expansion part 461 is disposed at the position corresponding to each volume variation part 441. Namely, the expansion part 461 is disposed between the volume variation part 441 of the first internal tube 44a and the volume variation part 441 of the second internal tube 43b. The expansion part 461 disposed at such a position has a thickness (tube wall) set thinner than that of the region in the periphery thereof (therearound). As a result, when the gas G is supplied (flows) into the expansion part 461, the expansion part 461 expands. Whereas, when the supply of the gas G is stopped, the expansion part 461 shrinks. The expansion part 461 functions as a deformation means for deforming each volume variation part 441 so as to vary the volume through expansion/shrinkage.

Figure 10:
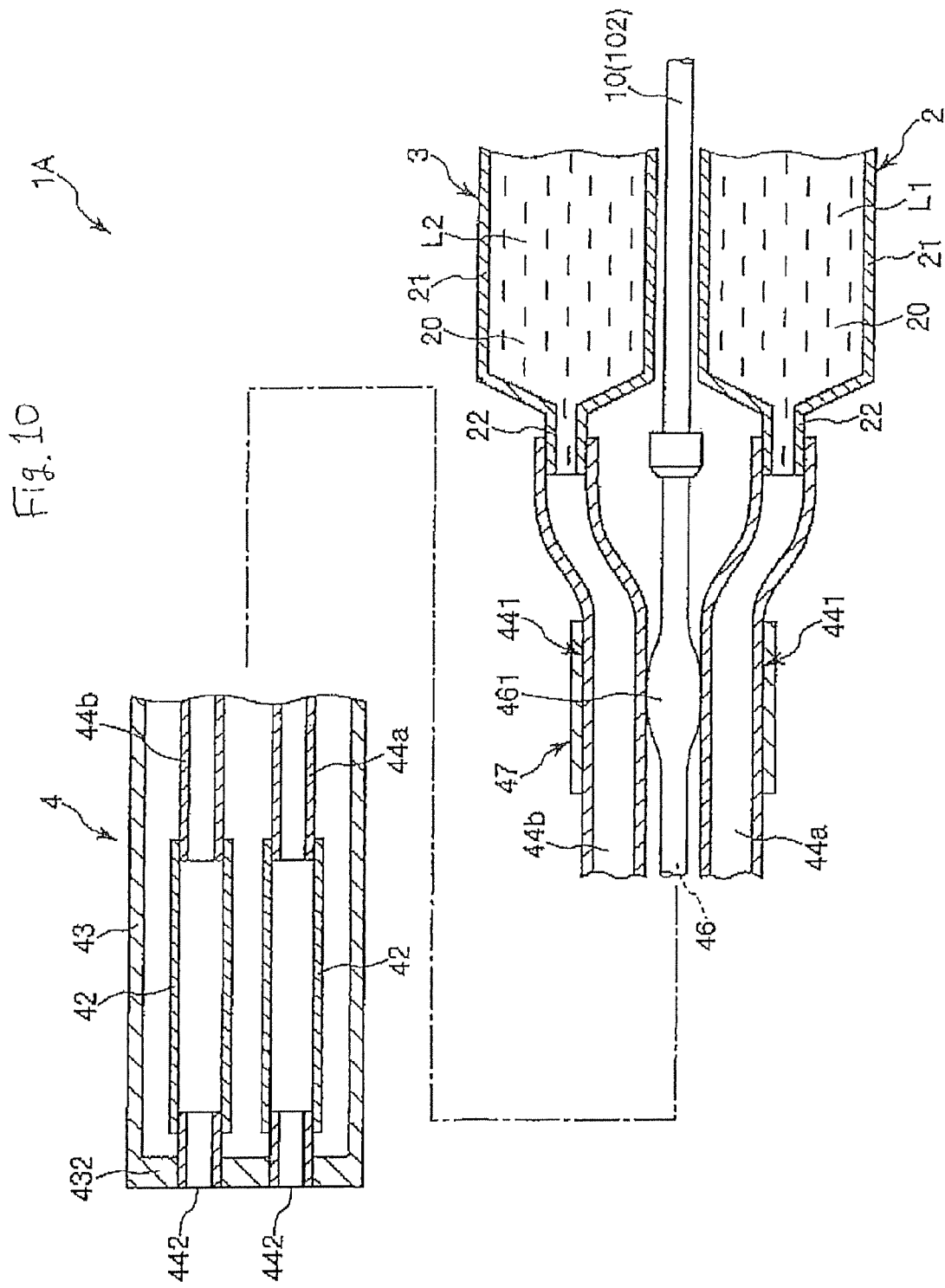
FIG. 10 is a fragmentary longitudinal cross-sectional view of the nozzle and syringe of the sprayer according to a second embodiment, illustrating parts of the sprayer in an operational state.
Figure 14:
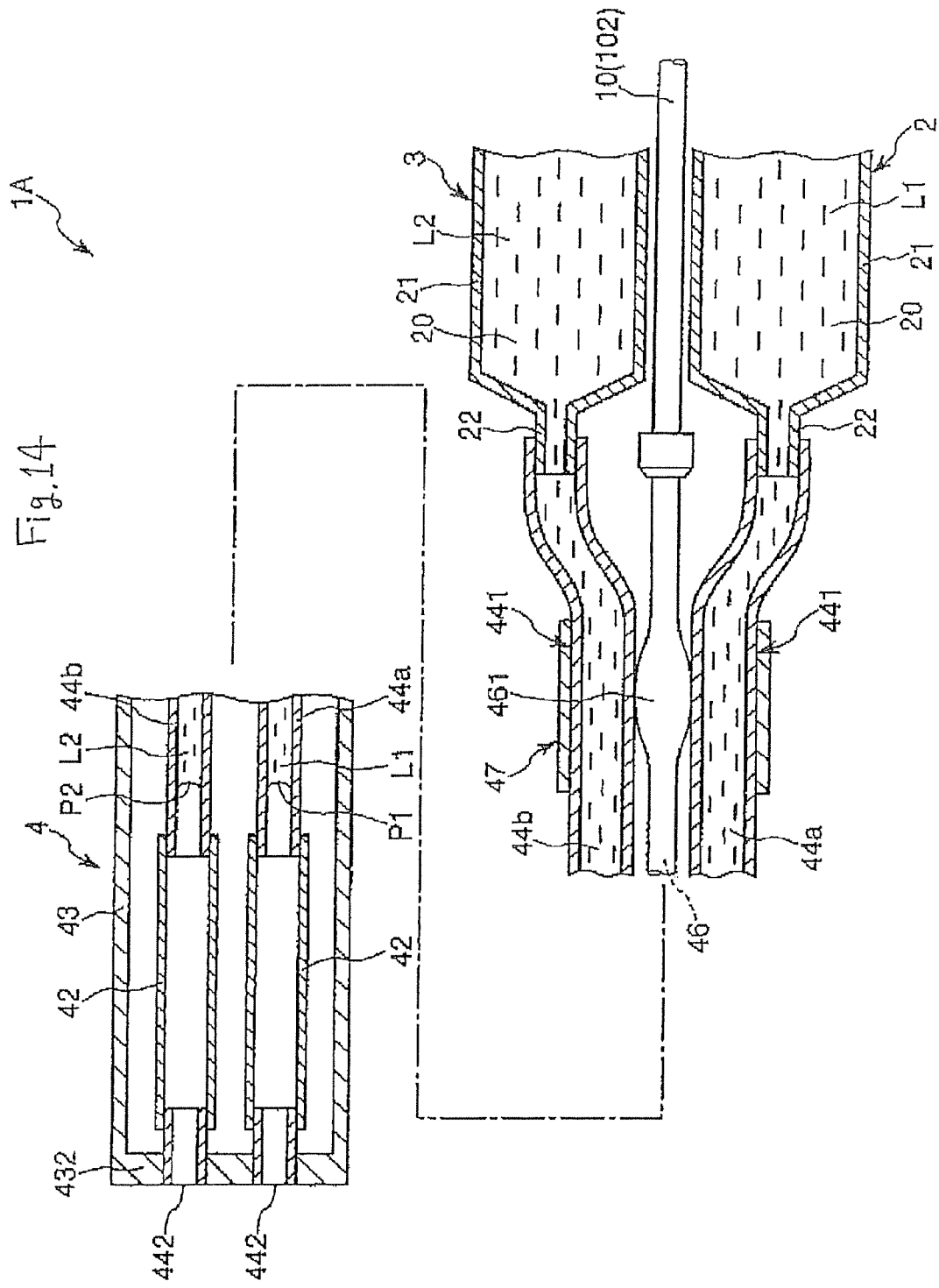
FIG. 14 is a fragmentary longitudinal cross-sectional view of the nozzle and syringe of the sprayer according to the second embodiment, illustrating parts of the sprayer in another operational state.

As shown in FIGS. 10 and 14, the expansion part 461 has an outer diameter a little larger than the external diameter of the supply tube 46 in a natural state (or most shrunk state). Further, in this state, the expansion part 461 may be in contact with respective volume variation parts 441 to such an extent as not to press respective ones respectively, or may be separated from respective volume variation parts 441, respectively.

With the configuration shown in FIGS. 10 and 14, the expansion part 441 is in contact with respective volume variation parts 441 respectively to such a degree as not to press against them. At this step, respective volume variation parts 441 have been maximized in volume, respectively. Incidentally, the term "natural state" denotes the state in which an external force is not applied, namely the state in which the gas G is not supplied in the inside.

Figure 11:
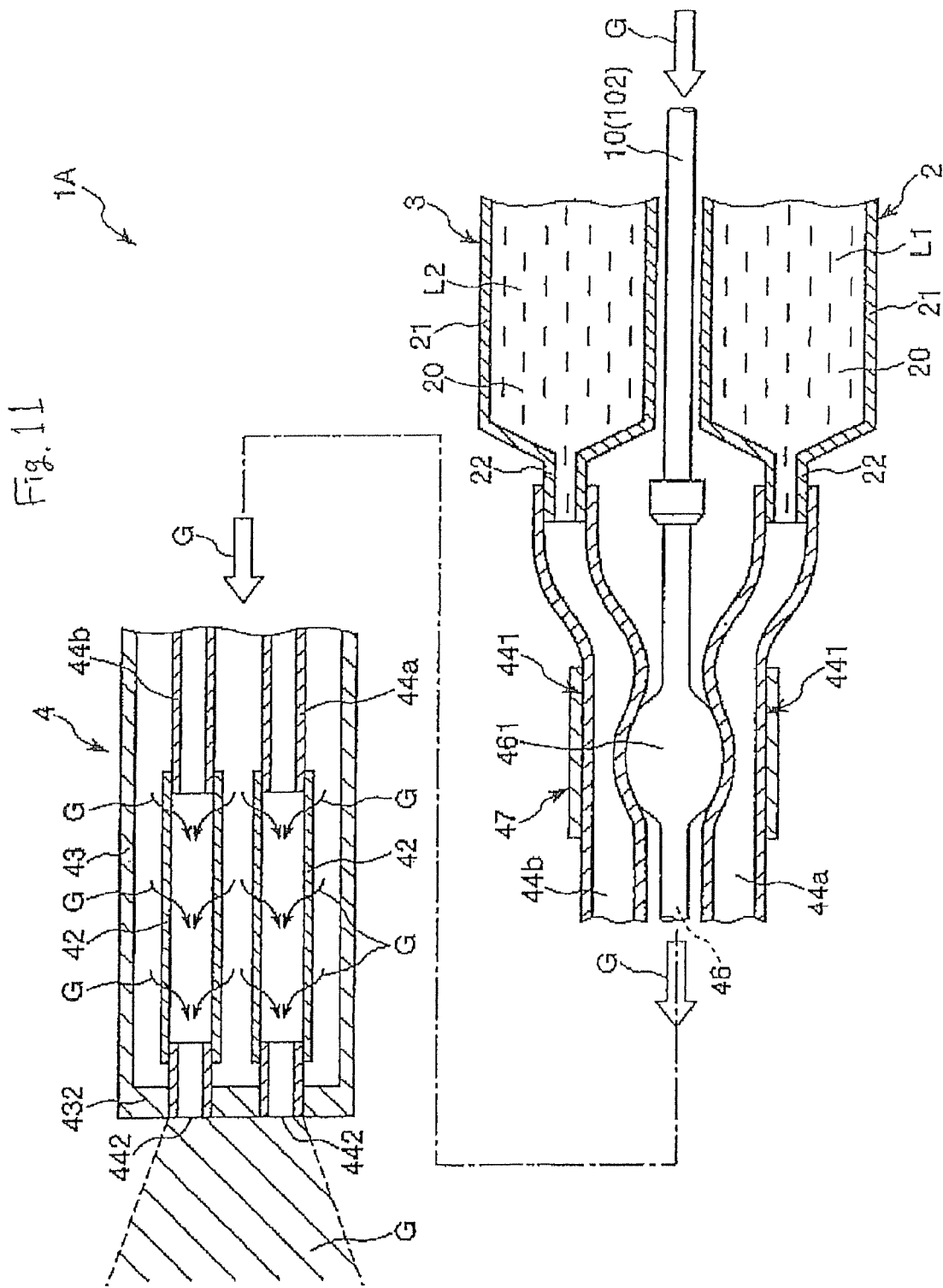
FIG. 11 is a fragmentary longitudinal cross-sectional view of the nozzle and syringe of the sprayer according to the second embodiment, illustrating parts of the sprayer in another operational state.
Figure 12:
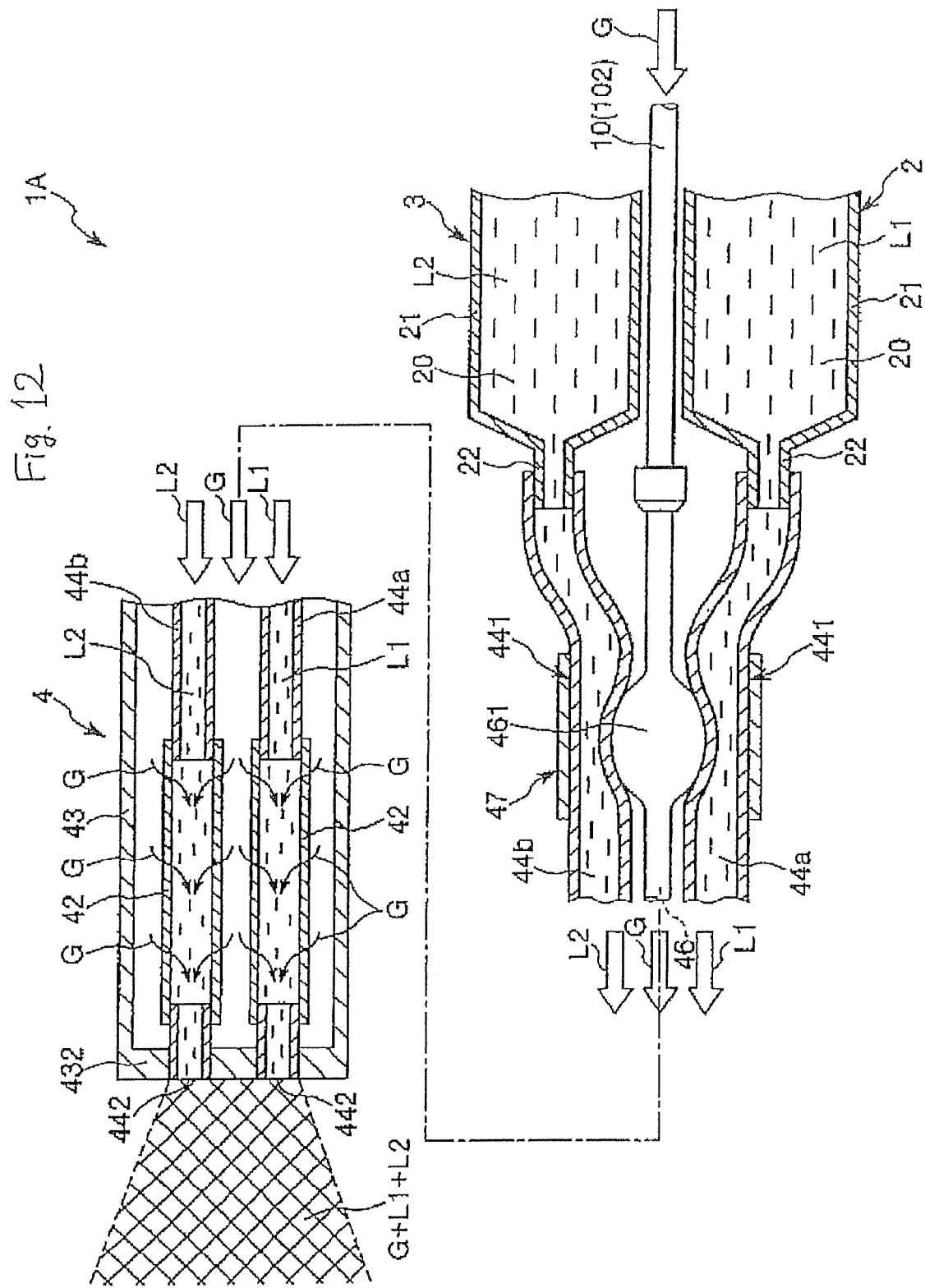
FIG. 12 is a fragmentary longitudinal cross-sectional view of the nozzle and syringe of the sprayer according to the second embodiment, illustrating parts of the sprayer in another operational state.
Figure 13:
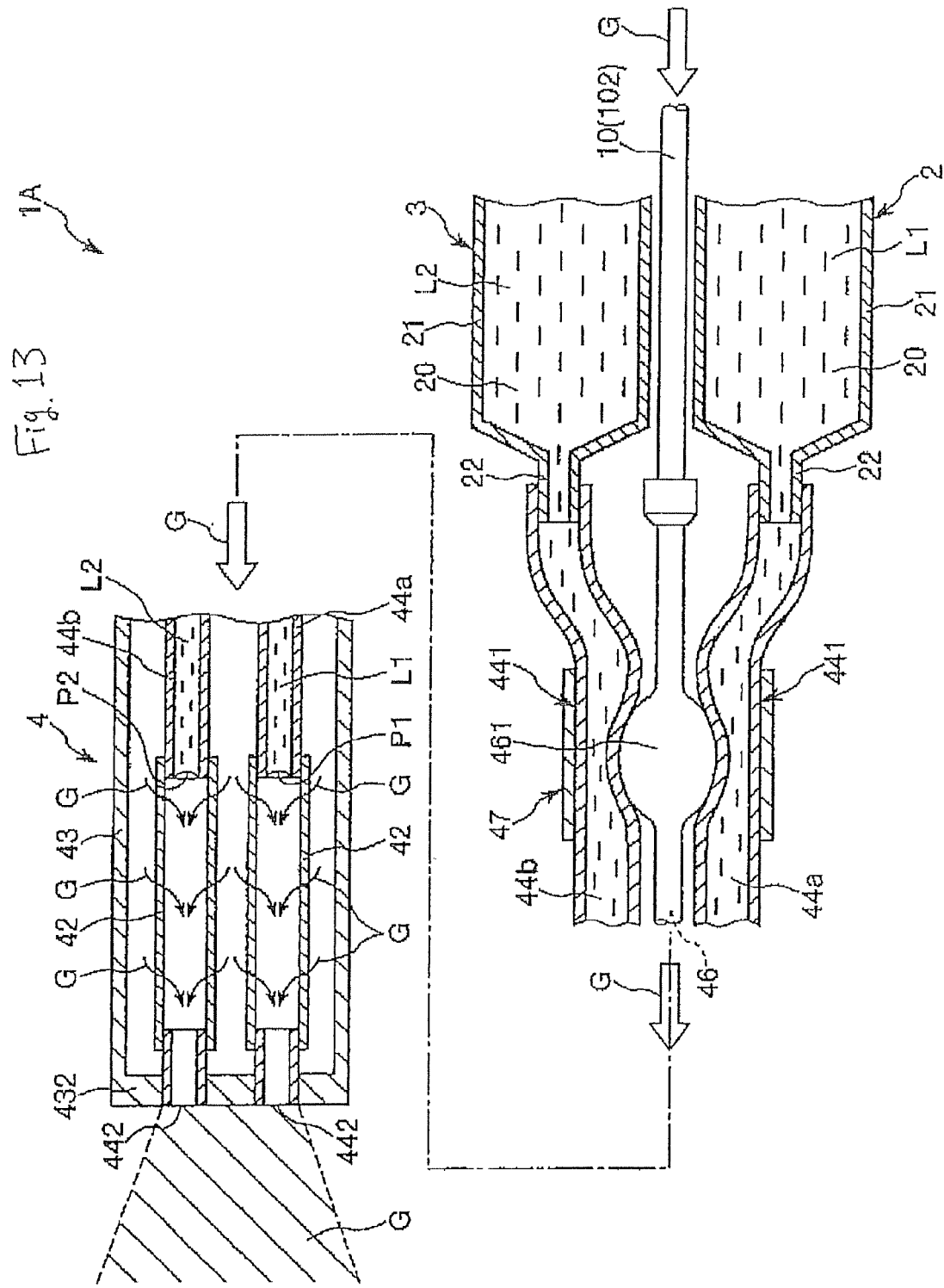
FIG. 13 is a fragmentary longitudinal cross-sectional view of the nozzle and syringe of the sprayer according to the second embodiment, illustrating parts of the sprayer in another operational state.

As shown in FIGS. 11-13, when a gas is supplied to the supply tube 46, the gas is also supplied to the inside of the expansion part 461, so that the expansion part 461 expands. The expanded expansion part 461 compresses the volume variation part 441 against their respective elastic forces of respective volume variation parts 441. This results in a reduction of each volume of respective volume variation parts 441. The degree of pressing of the expanded expansion part 461 against respective volume variation parts 441 is set at such a degree as not to bring the internal circumferential surfaces into close contact with each other in each volume variation part 441.

Further, when the expanded expansion part 461 has shrunk again or returned toward its contracted state, the compression against each volume variation part 441 is released. As a result, respective volume variation parts 441 return to their original states by their own respective elasticities as shown in FIG. 9.

Further, the nozzle 4 has a ring (annular band) 47 for externally collectively holding, in a circumferential manner, the volume variation part 441 of the first internal tube 44a, the volume variation part 441 of the second internal tube 44b, and the expansion part 461. The ring 47 is formed by winding a band-shaped body formed of, for example, a plastic material. The positional relationship of both the volume variation parts 441 and the expansion part 461 is regulated by the ring 47 irrespective of the expansion/shrinkage of the expansion part 461. As a result, when the expansion part 461 expands, respective volume variation parts 441 are pressed by the expanded expansion part 461, respectively.

Thus, with the sprayer 1A, respective volumes of the volume variation parts 441 change by the expansion/shrinkage of the expansion part 461.

Set forth below is a description of the operation state of the sprayer 1A in a usable state, i.e., with the first syringe 2 filled with the first liquid L1 and the second syringe 3 filled with the second liquid L2 mounted in the sprayer, and connected to the cylinder 300.

In the sprayer 1A shown in FIG. 10, the state prior to the operation of the operation part 8 is the same state as with the sprayer 1 described in the first embodiment. Further, with the sprayer 1A of this second embodiment, the expansion part 461 is not expanded, and hence the compression against respective volume variation parts 441 does not occur.

Then, with the sprayer 1A in this state, the pressing part 82 is pressed and operated with a thumb, and the second connection part 92 is tilted. As a result, the gap 98 is caused between the sealing member 94 and the flange part 95. Thus, the gas G passes through the gap 98 and is able to flow towards the nozzle in a manner similar to that shown in FIG. 4. As a result, the gas G flows into the supply tube 46 through the second tube 102, and thereby passes into the inside of the external tube 43. Then, when the gas G reaches the vicinity of the gas permeable films 42, it flows into the first internal tube 44a and the second internal tube 44b through the gas permeable film 42. The gas G is ejected at high speed from each ejection port 442 as generally shown in FIG. 11. At this step, the expansion part 461 expands, so that the respective volume variation parts 441 are respectively compressed by the expansion of the expansion part 461. The expansion of the expansion part 461 is maintained until the supply of the gas G to the expansion part 461 is stopped.

The pressing operation on the pressing part 82 by the user's thumb falls short of moving the whole operation part 8. That is, the pressing force applied by the user's thumb does not cause the plungers 26 to move in the direction of the distal end. For this reason, the first liquid L1 and the second liquid L2 are not yet supplied to the first internal tube 44a and the second internal tube 44b, respectively.

As the pressing part 82 is further pressed, the second connection part 92 is tilted to the limit, so that the pressing force from the thumb is transferred to the connection part 81 via the pressing part 82. As a result, the connection part 81 (the whole operation part 8) starts to move. Accordingly, the first liquid L1 is pushed out from the first syringe 2, and the second liquid L2 is also pushed out from the second syringe 3. The pushed first liquid L1 passes through the volume variation part 441 still being compressed by the expansion part 461, further merges with the gas G in the gas permeable film 42, and is ejected from the ejection port 442 of the first internal tube 44a together with the gas G as depicted in FIG. 12. In a manner similar to the first liquid L1, the second liquid L2 passes through the volume variation part 441 still being compressed by the expansion part 461, further merges with the gas G in the gas permeable film 42, and is ejected from the ejection port 442 of the second internal tube 44b together with the gas G as shown in FIG. 12.

As described above, the first liquid L1 and the second liquid L2 ejected from respective ejection ports 442 are respectively atomized, and mutually mixed together to be sprayed onto the affected part.

After completion of spraying of the mixture in a prescribed amount onto the affected part, the pressing force against the pressing part 82 (operation part 8) of the thumb is eased. Then, the movement of the whole operation part 8 is stopped. This stops the movement of each plunger 26, so that ejection of the first liquid L1 and the second liquid L2 is individually stopped as seen in FIG. 13. At this time, the second posture of the second connection part 92 by pressing of the pressing part 82 is maintained, and hence the gas G continues to be ejected as shown in FIG. 13. Accordingly, as described above, the first liquid L1 at the portion closer to the distal end than the gas permeable film 42 in the first internal tube 44a is pushed out of the ejection port 442 by the gas G which has flowed through the gas permeable film 42. The second liquid L2 at the portion closer to the distal end than the gas permeable film 42 in the second inner tube 44b is pushed out of the ejection port 442 by the gas G which has flowed through the gas permeable film 42. This prevents the first liquid L1 and the second liquid L2 from remaining in the vicinity of their respective ejection ports 442. As a result, clogging is inhibited or prevented from occurring at the respective ejection ports 442.

Finally, when the pressing force against the pressing part 82 by the thumb is eased, the thumb which has pressed the pressing part 82 is separated from the pressing part 82. As a result, the pressing force against the second connection part 92 is released. Thus, the second connection part 92 returns to the first posture. As a result, the gap 98 between the sealing member 94 and the flange part 95 disappears. That is, the sealing member 94 and the entire circumference of the peripheral part 951 of the flange part 95 come in close contact with each other in the manner shown in FIG. 3. At this point, supply of the gas G to the supply tube 46 is stopped as illustrated in FIG. 14.

When the supply of the gas G to the supply tube 46 is stopped, the expansion part 461 shrinks as illustrated in FIG. 14. As a result, the compression of the expansion part 461 against each volume variation part 441 is released. Accordingly, the volume of each volume variation part 441 becomes larger (increases) than the volume in the state in which the liquid (the first liquid L1 or the second liquid L2) is ejected. The increase in volume causes the distal end P1 of the first liquid L1 to be further drawn closer to the rear end (i.e., toward the rear direction) than the distal end P1 of the first liquid L1 in the first embodiment (the state shown in FIG. 9). the distal end P2 of the second liquid L2 is also further drawn closer to the rear end (i.e., in the rear direction) than the distal end P2 of the second liquid L2 in the first embodiment (in the state shown in FIG. 9).

With this construction, upon completing the spraying operation with the sprayer 1A, the distal end P1 of the first liquid L1 and the distal end P2 of the second liquid L2 are situated at more distant positions from their respective ejection ports 442, respectively. This can help prevent the first liquid L1 and the second liquid L2 from being mixed together, and solidifying in the vicinity of the ejection port 442 of the first internal tube 44a and the ejection port 442 of the second internal tube 43b. As a result, it is possible to prevent clogging (deposition of the solidified product of the mixture of the first liquid L1 and the second liquid L2) from occurring at the ejection port 442 of the first internal tube 44a and the ejection port 442 of the second internal tube 44b after use of (after spraying of) the sprayer 1A. The sprayer 1A can thus be used for spraying to the affected part again.

Figure 15:
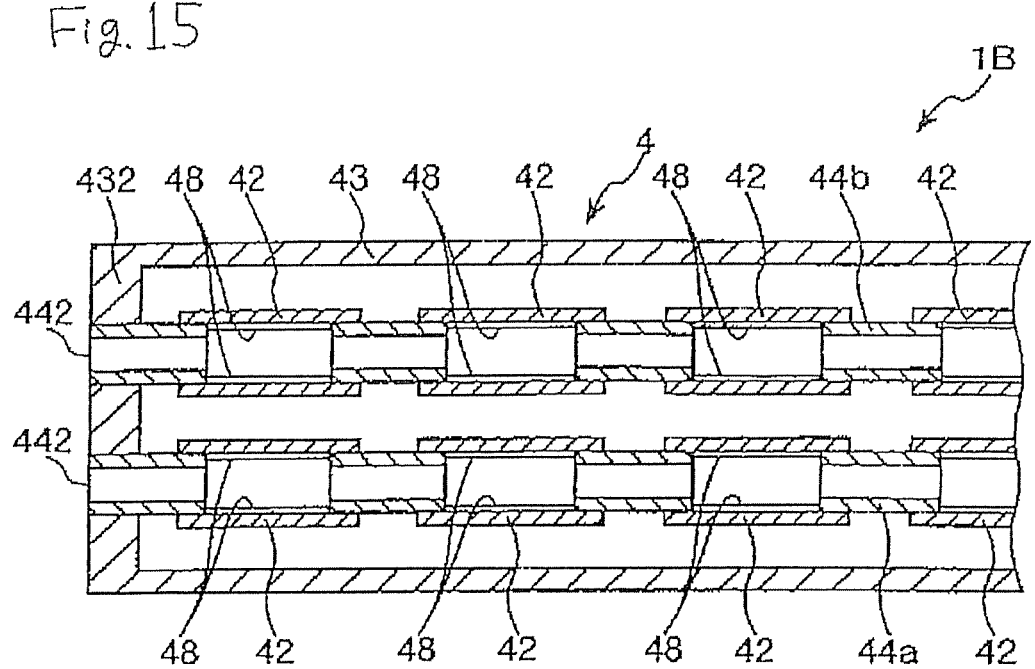
FIG. 15 is a fragmentary longitudinal cross-sectional view of the nozzle and syringe of the sprayer according to the second embodiment, illustrating parts of the sprayer in another operational state.
Figure 16:
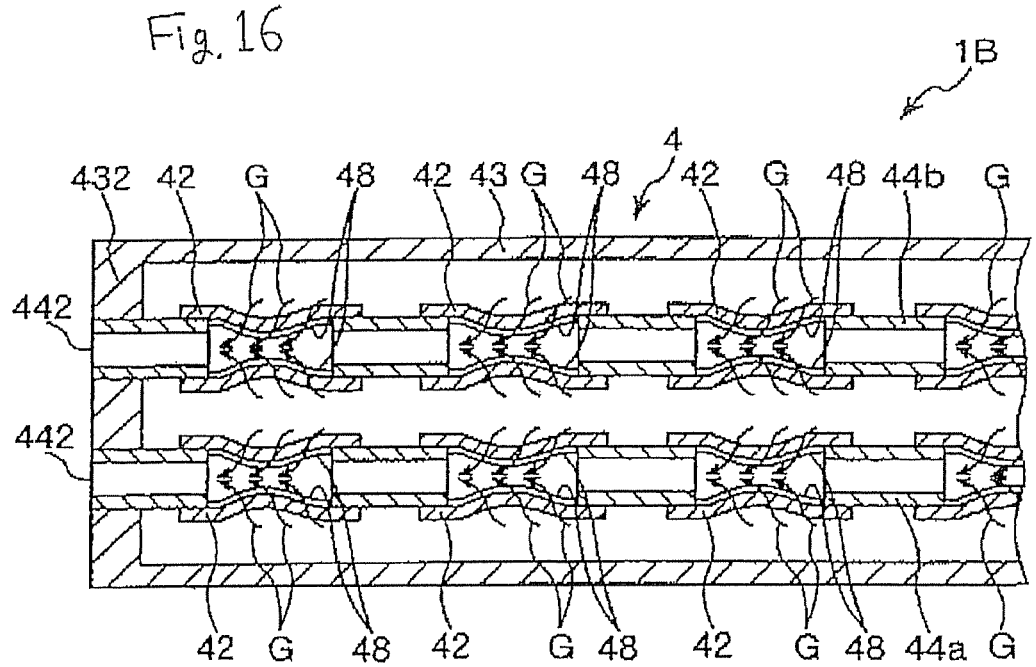
FIG. 16 is a fragmentary longitudinal cross-sectional view of the nozzle and syringe of the sprayer according to a third embodiment, illustrating parts of the sprayer in an operational state.
Figure 17:
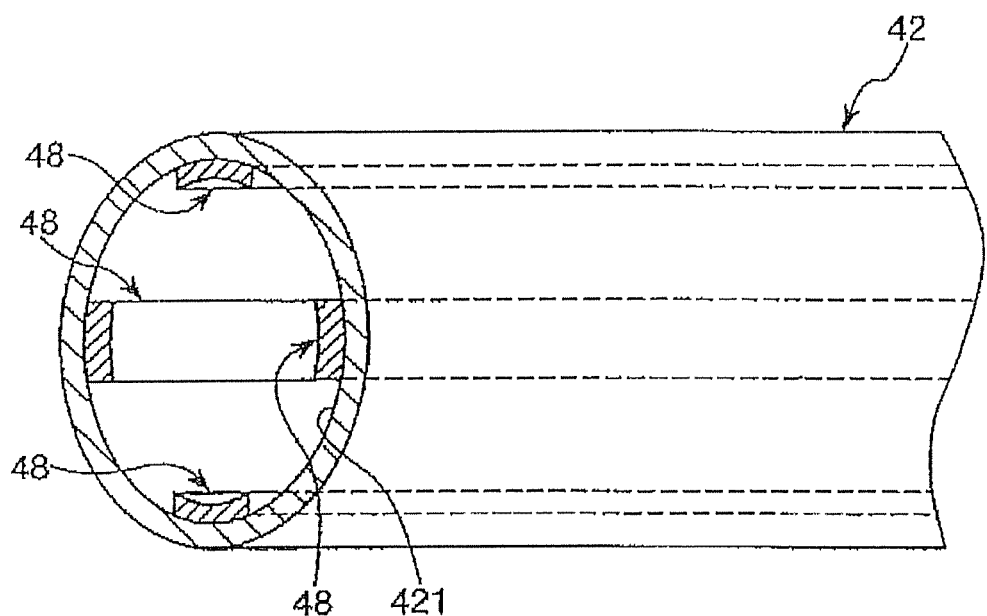
FIG. 17 is a transverse cross-sectional perspective view of a gas permeable film of the nozzle of the sprayer shown in FIG. 15.

FIGS. 15-17 illustrate aspects of the nozzle and syringe in a sprayer according to a third embodiment. Features in this embodiment that are the same as those in the first embodiment are designated by the same reference numeral, and a detailed description of such features is not repeated. The description below will primarily describe differences in this embodiment relative to the embodiments described above.

The third embodiment of the sprayer disclosed here is the same as the first embodiment, except that the arrangement of the gas permeable films is different.

The sprayer 1B shown in FIGS. 15 and 16 includes a plurality of gas permeable films 42 set in the first internal tube 44a and the second internal tube 43b. The gas permeable films 42 are arranged intermittently or in spaced apart relation to one another (at equal intervals) along the longitudinal direction of the first internal tube 44a. This description also applies to the second internal tube 44b.

Each gas permeable film 42 possesses flexibility by appropriately setting, for example, the thickness of the wall part or the constituent material forming the gas permeable film. As shown in FIG. 16, when the gas G is supplied into the external tube 43, the pressure in the external tube 43 increases (an external force is applied), so that warp is caused in the central part in the longitudinal direction of each gas permeable film 42. That is, the internal diameter of the central part in the longitudinal direction of each gas permeable film 42 decreases. The degree of pressing against each gas permeable film 42 by external pressure is set at such so that the internal circumferential surfaces 421 of each gas permeable film 42 are not brought into close contact with each other. When each gas permeable film 42 decreases in diameter, the minimum internal diameter is preferably roughly equal to the internal diameter of the first internal tube 44a in front of and behind the gas permeable films 42 as generally shown in FIG. 16. The same also applies to the second internal tube 44b.

As shown in FIG. 17, on the internal circumferential surface 421 of each gas permeable film 42, a plurality of (four in this embodiment) elongated or long-shaped elastic pieces (elastic bodies) 48 are bonded (set). The bonding method by which the elongated pieces 42 are bonded to the inner circumferential surface of the gas permeable film 42 is not particularly limited. However, examples may include the methods of fusion (heat fusion, high frequency fusion, ultrasonic fusion, and the like), and adhesion (adhesion by an adhesive or a solvent).

The elastic pieces 48 are disposed at an equal angular interval along the circumferential direction of the internal circumferential surface 421 of the gas permeable film 42, namely, around the central axis of the gas permeable film 42. The gas permeable film 42 which is warped as described above upon supply of the gas G into the external tube 43 returns to the state shown in FIG. 15 by the elastic force (urging force (restoring force)) of each elastic piece 48 when the supply of the gas G is stopped (upon release of the external force).

Thus, in the sprayer 1B, each gas permeable film 42 is configured such that its internal volume varies.

As described above, when the first liquid L1 and the second liquid L2 are ejected, and then stop being ejected, each gas permeable film 42 is rendered in the state shown in FIG. 16. In this state, the first liquid L1 at a portion closer to the distal end than the gas permeable film 42 situated at least closest to the distal end of the first internal tube 44a is pushed out of the ejection port 442 by the gas G which has flowed through each gas permeable film 42. The second liquid L2 at a portion closer to the distal end than the gas permeable film 42 situated at least closest to the distal end of the second internal tube 44b is pushed out of the ejection port 442 by the gas G which has flowed through each gas permeable film 42. This inhibits or prevents the first liquid L1 and the second liquid L2 from remaining in the vicinity of their respective ejection ports 442. As a result, clogging is inhibited or prevented from occurring at the respective ejection ports 442.

Then, upon stopping the supply of the gas G, each gas permeable film 42 individually returns to the state shown in FIG. 15 from the state shown in FIG. 16 as described above. During this time, the volume of each gas permeable film 42 increases. Accordingly, even when the first liquid L1 remains in the region including the gas permeable films 42 of the first internal tube 44a, the first liquid L1 can be further drawn toward the proximal end (the same also applies to the second internal tube 44b). As a result, the distal end P1 of the first liquid L1 and the distal end P2 of the second liquid L2 are situated at more distant positions from their respective ejection ports 442, respectively. This can help prevent the first liquid L1 and the second liquid L2 from being mixed, and gelating in the vicinity of the ejection port 442 of the first internal tube 44a and the ejection port 442 of the second internal tube 43b. As a result, it is possible to inhibit or prevent clogging.

The material forming each elastic piece 48 is not particularly limited. As examples, the same materials as the materials for the gasket 24 described in the first embodiment can be used.

Figure 18:
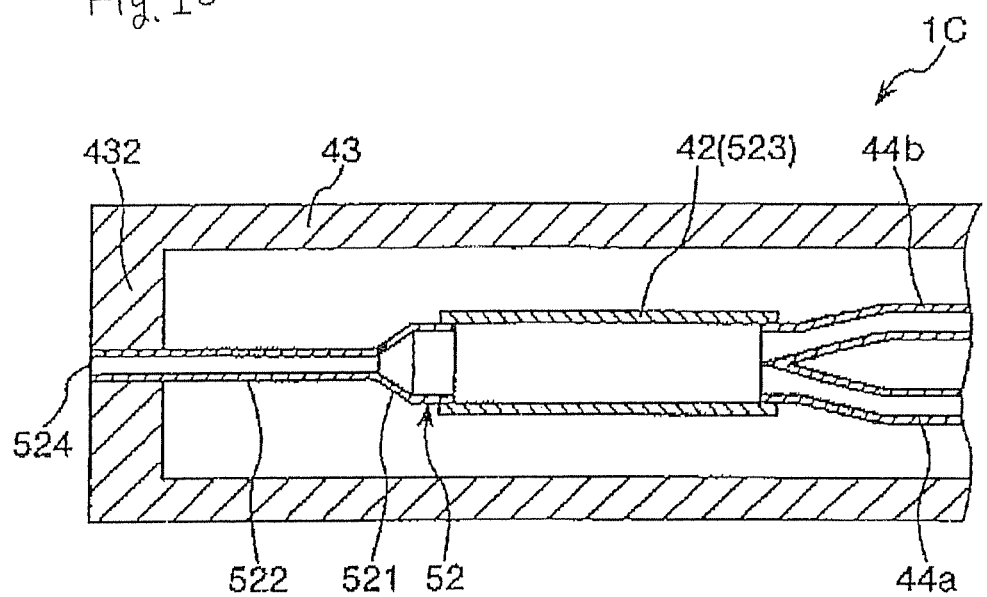
FIG. 18 is a fragmentary longitudinal cross-sectional view of the nozzle and syringe of the sprayer according to a fourth embodiment, illustrating parts of the sprayer in an operational state.
Figure 19:
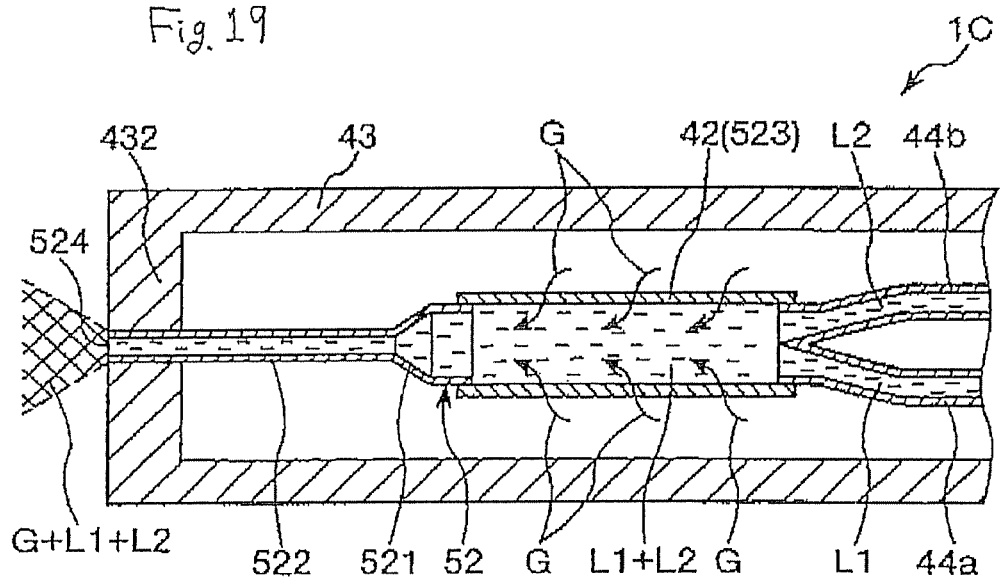
FIG. 19 is a fragmentary longitudinal cross-sectional view of the nozzle and syringe of the sprayer according to the fourth embodiment, illustrating parts of the sprayer in another operational state.
Figure 20:
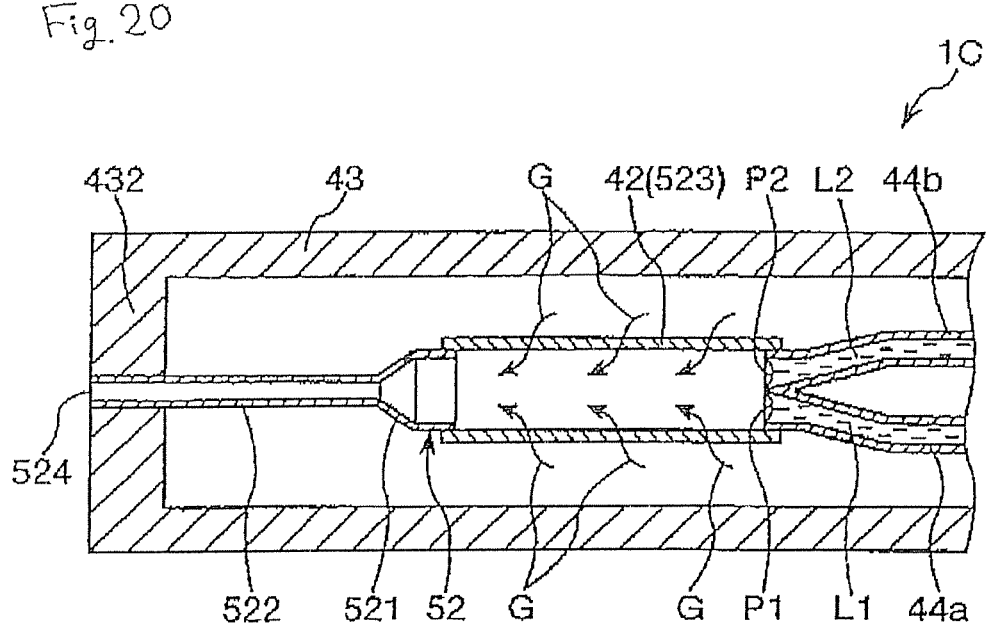
FIG. 20 is a fragmentary longitudinal cross-sectional view of the nozzle and syringe of the sprayer according to the fourth embodiment, illustrating parts of the sprayer in another operational state.

FIGS. 18-20 illustrate aspects of the nozzle and syringe in a sprayer according to a third embodiment. Features in this embodiment that are the same as those in the first embodiment are designated by the same reference numeral, and a detailed description of such features is not repeated. The description below will primarily describe differences in this embodiment relative to the embodiments described above.

This embodiment is the same as the first embodiment, except that the configuration of the internal tubes is different.

In the sprayer 1C shown in FIGS. 18-20, the first internal tube 44a and the second internal tube 44b merge with each other at the portion on the distal end side (the distal end) thereof. This results in the formation of a merge part 52 at which the internal spaces of the respective internal tubes merge with each other.

The merge part 52 has a taper part 521 gradually decreasing in internal diameter toward the distal end direction. By way of the taper part 521, the merge part 52 is divided into a small diameter part 522 with a small internal diameter on the distal end side, and a large diameter part 523 with a large internal diameter on the proximal end side. The distal end opening of the small diameter part 522 functions as an ejection port 524 for ejecting the liquid mixture (a mixture of the first liquid L1 and the second liquid L2) together with the gas G as depicted in FIG. 19.

With the sprayer 1C thus configured, the first liquid L1 and the second liquid L2 merge at the merge part 52 to be uniformly mixed with each other, resulting in a liquid mixture. Further, the liquid mixture is, as described above, atomized, and ejected.

Further, the large diameter part 523 of the merge part 52 is formed over the majority of its extent of the gas permeable film 42. As a result, the portion on the proximal end side (proximal end part) of the merge part 52 can be formed of the gas permeable films 42. As a result, upon stopping the ejection of the first liquid L1 and the second liquid L2 by the operation of the operation part 8, the liquid mixture in the merge part 52 can be blown away from the ejection port 524 by the gas G which has flowed into the merge part 52 through the gas permeable films 42 (see FIG. 20).

As shown in FIG. 19, when the liquid mixture is being ejected, the gas G which has passed through the gas permeable films 42 becomes microbubbles (air bubbles) in the liquid mixture passing through the merge part 52. Due to the microbubbles, the liquid mixture is stirred in the process of passing through the merge part 52. As a result, the first liquid L1 and the second liquid L2 are uniformly mixed with each other to be a liquid mixture, and sprayed. Particularly, when the viscosities of both the liquids are different from each other, the liquids are less likely to be a uniform liquid mixture merely by the merging of the liquids. However, with the sprayer here as described above, the microbubbles exert a stirring action involving stirring the first liquid L1 and the second liquid L2, and promoting mixing thereof. This results in a more uniform liquid mixture.

In this embodiment, the merge part 52 is formed of the gas permeable film 42 at the portion on the proximal end side thereof. However, the configuration is not limited in this regard. for example, the entire merge part 52 may be formed of the gas permeable film 42.

Figure 21:
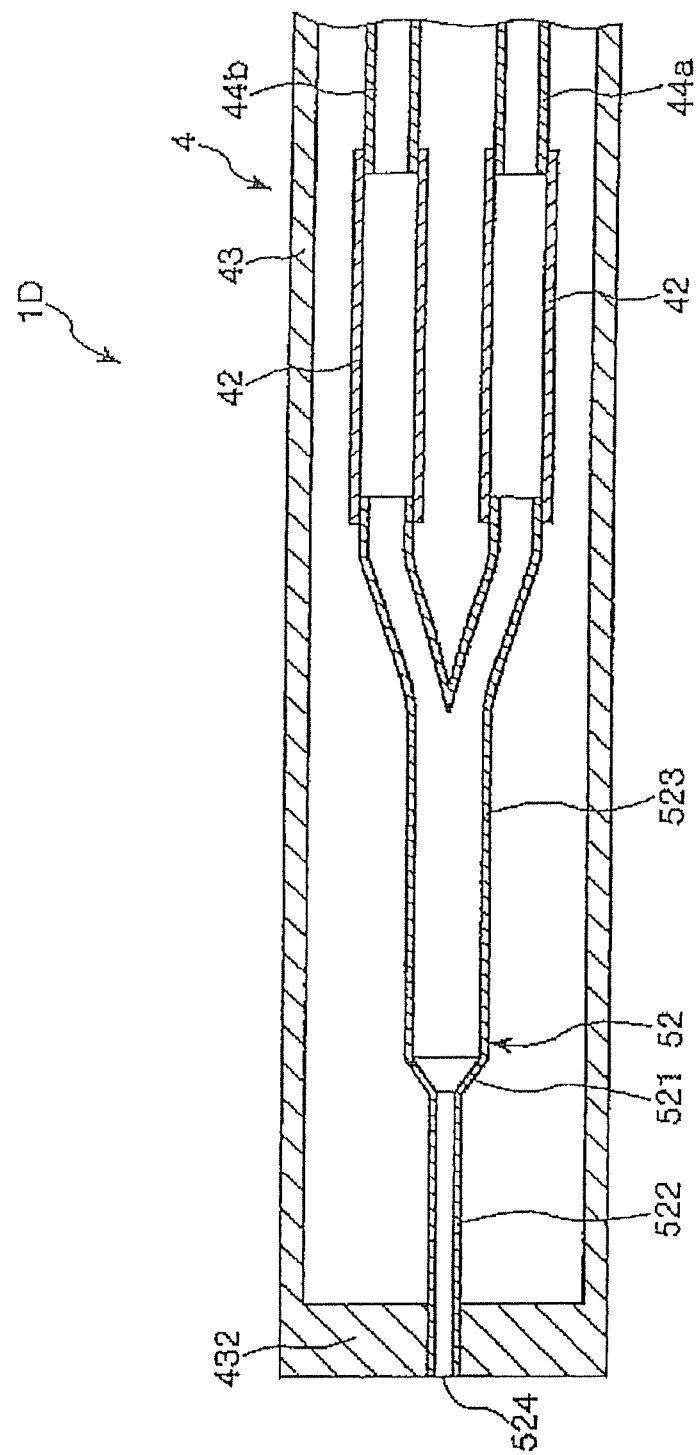
FIG. 21 is a longitudinal cross-sectional view of a nozzle of a sprayer according to a fifth embodiment disclosed here.

FIG. 21 illustrates aspects of the nozzle and syringe in a sprayer according to a fifth embodiment. Features in this embodiment that are the same as those in the embodiments described above are designated by the same reference numeral, and a detailed description of such features is not repeated. The description below will primarily describe differences in this embodiment relative to the embodiments described above.

This embodiment is the same as the fourth embodiment, except that the setting position of each gas permeable film 42 is different.

In the sprayer 1D shown in FIG. 21, respective gas permeable films 42 are set in the first internal tube 44a and the second internal tube 44b, respectively. The respective gas permeable films 42 are set in the vicinity of the merge part 52.

With the sprayer 1D thus configured, the operation of the operation part 8, upon stopping the ejection of the first liquid L1 and the second liquid L2, the gas G which has flowed through respective gas permeable films 42 can blow away not only the liquid mixture in the merge part 52 but also the first liquid L1 in the first internal tube 44a (gas permeable film 42) and the second liquid L2 in the second internal tube 44b (gas permeable film 42) from the ejection port 524. This can help prevent the first liquid L1 and the second liquid L2 from remaining in the ejection port 524, and causing clogging in the ejection port 524.

In the embodiment shown in FIG. 21, the gas permeable films 42 are provided in both the first internal tube 44a and the second internal tube 44b. However, the configuration is not limited in this regard. For example, the gas permeable film 42 may be set in one of the two tubes (the first internal tube 44a or the second internal tube 44b). As an example, with the gas permeable film 42 set in only the first internal tube 44a, by the operation of the operation part 8, and upon stopping the ejection of the first liquid L1 and the second liquid L2, the gas G which has flowed into the first internal tube 44a through the gas permeable film 42 on the first internal tube 44a side blows away the liquid mixture in the merge part 52, and the first liquid L1 in the first internal tube 44a (gas permeable film 42) from the ejection port 524. At this time, the pressure in the second internal tube 44b communicating with the merge part 52 decreases. Accordingly, the second liquid L2 in the second internal tube 44b also flows into the merge part 52, and is blown away from the ejection port 524. This can inhibit or prevent the first liquid L1 and the second liquid L2 from remaining in the ejection port 524, and causing clogging in the ejection port 524.

Figure 22:
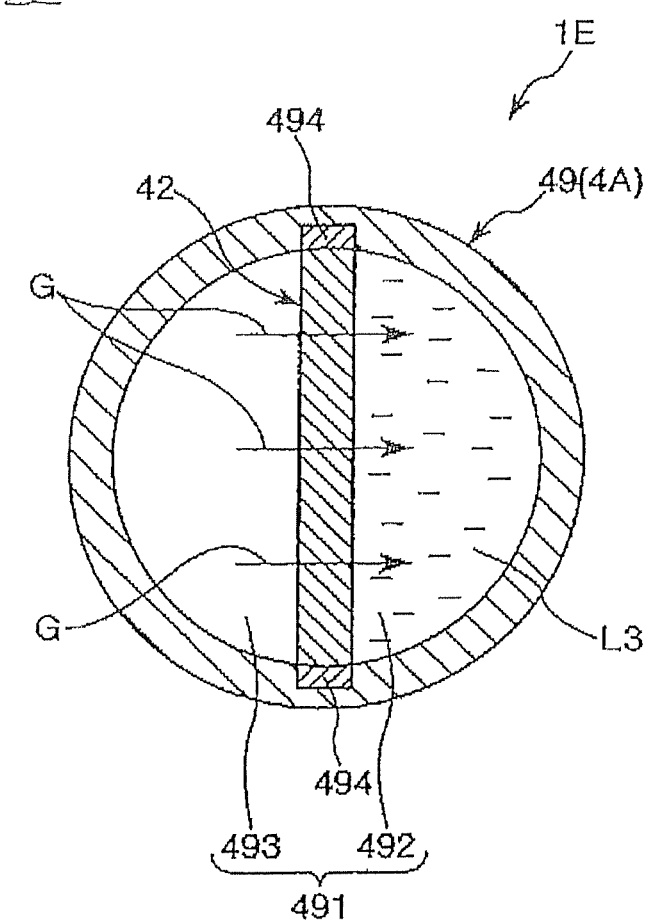
FIG. 22 is a transverse cross-sectional view of the distal end part of the nozzle of a sprayer according to a sixth embodiment disclosed here.

FIG. 22 illustrates aspects of the nozzle and syringe in a sprayer according to a sixth embodiment. Features in this embodiment that are the same as those in the embodiments described above are designated by the same reference numeral, and a detailed description of such features is not repeated. The description below will primarily describe differences in this embodiment relative to the embodiments described above.

This sixth embodiment is the same as the first embodiment, except that the number of internal tubes and the configuration of the internal tubes is different. Each sprayer of the first to fifth embodiments is configured such that two syringes are accommodated, and two types of liquids different in liquid composition are ejected from respective syringes while being mixed. The sprayer of this embodiment is configured such that one syringe is mounted in the sprayer, and one type of liquid L3 is ejected from the syringe.

In the sprayer 1E shown in FIG. 22, a nozzle 4A is formed of one tube-like body 49 (single tube). In the tube-like body 49, in a transverse cross sectional view, the bore 491 is compartmentalized into two spaces or two passages by a gas permeable film 42. One space of the two compartmented spaces functions as a liquid flow path 492 through which a liquid passes, while the other space functions as a gas flow path 493 through which a gas G passes.

The gas permeable film 42 is bonded and fixed to the internal circumferential part of the tube-like body 49 by, for example, an adhesive. Also with the sprayer 1E thus configured, as with the sprayers of the first to fifth embodiments, clogging is inhibited or prevented from occurring in the nozzle.

Incidentally, the nozzle 4A in this embodiment may be the same double tube structure as that of each nozzle of the sprayers of the first to fifth embodiments.

Figure 23:
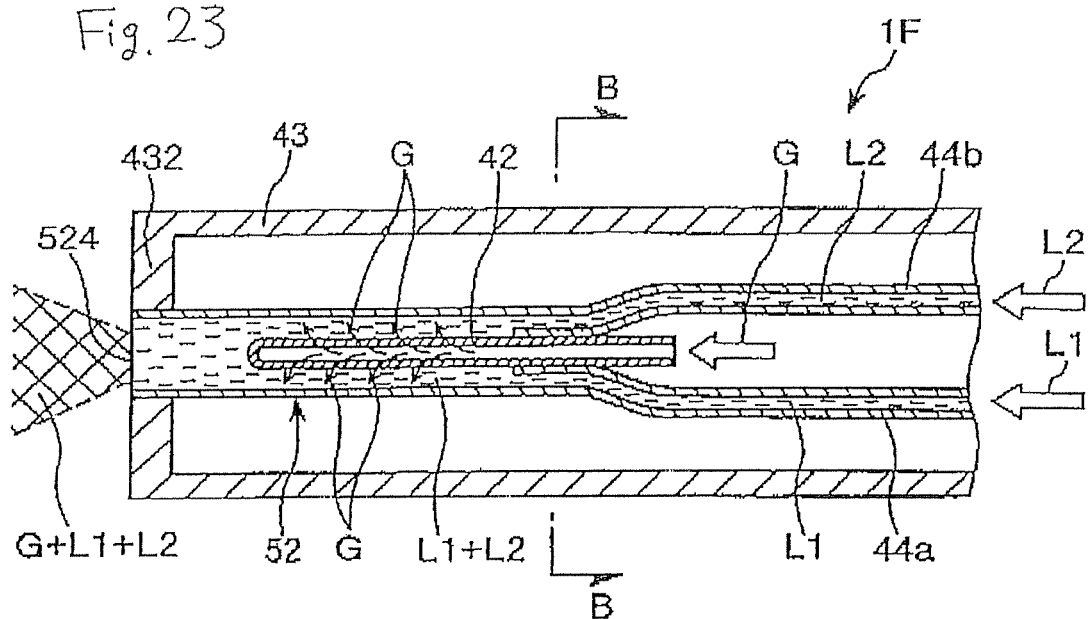
FIG. 23 is a longitudinal cross-sectional view of the distal end part of a nozzle of a sprayer according to a seventh embodiment disclosed here.
Figure 24:
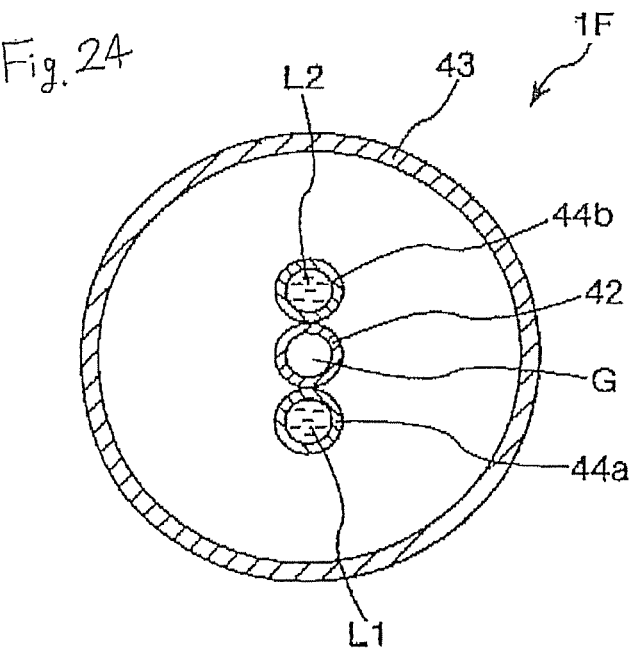
FIG. 24 is a cross-sectional view of the distal end part of the nozzle shown in FIG. 23 taken along the section line B-B in FIG. 23.

FIGS. 23 and 24 illustrate aspects of the nozzle and syringe in a sprayer according to a seventh embodiment. Features in this embodiment that are the same as those in the embodiments described above are designated by the same reference numeral, and a detailed description of such features is not repeated. The description below will primarily describe differences in this embodiment relative to the embodiments described above.

This embodiment is the same as the fourth embodiment, except that the setting position of the gas permeable film is different.

The gas permeable film 42 of the sprayer 1F shown in FIGS. 23 and 24 has an overall shape of a tube with a closed distal end. The gas permeable film 42 in such a shape is inserted from the proximal end side of the merge part 52 into the merge part 52 as shown in FIG. 23. Further, the gas permeable film 42 is disposed between the first internal tube 44a and the second internal tube 44b as illustrated in FIG. 24. The gas permeable films 42 may be disposed at a plurality of sites.

In the sprayer 1F, the gas G which has been supplied into the nozzle 4 by the operation of the operation part 8 enters from the portion on the proximal end side (the proximal end part) of the gas permeable film 42 into the gas permeable film 42. The gas G which enters the gas permeable film 42 flows from the portion exposed in the merge part 52 of the gas permeable film 42 into the merge part 52, and is ejected together with the first liquid L1 and the second liquid L2 to the outside.

Then, upon stopping the ejection of the first liquid L1 and the second liquid L2, the gas G flowing through the gas permeable film 42 can blow away the liquid mixture in the merge part 52 from the ejection port 524. This helps prevent the first liquid L1 and the second liquid L2 from remaining in the ejection port 524, and causing clogging in the ejection port 524. Further, there is an advantage that the gas permeable film 42 with a relatively small film area enables stirring of the liquid mixture with efficiency.

FIG. 22 illustrates aspects of the nozzle and syringe in a sprayer according to a eighth embodiment. Features in this embodiment that are the same as those in the embodiments described above are designated by the same reference numeral, and a detailed description of such features is not repeated. The description below will primarily describe differences in this embodiment relative to the embodiments described above.

This embodiment is the same as the fourth embodiment, except that the formation positions of the open ends respectively facing the merge part of respective liquid flow paths are different.

Figure 25:
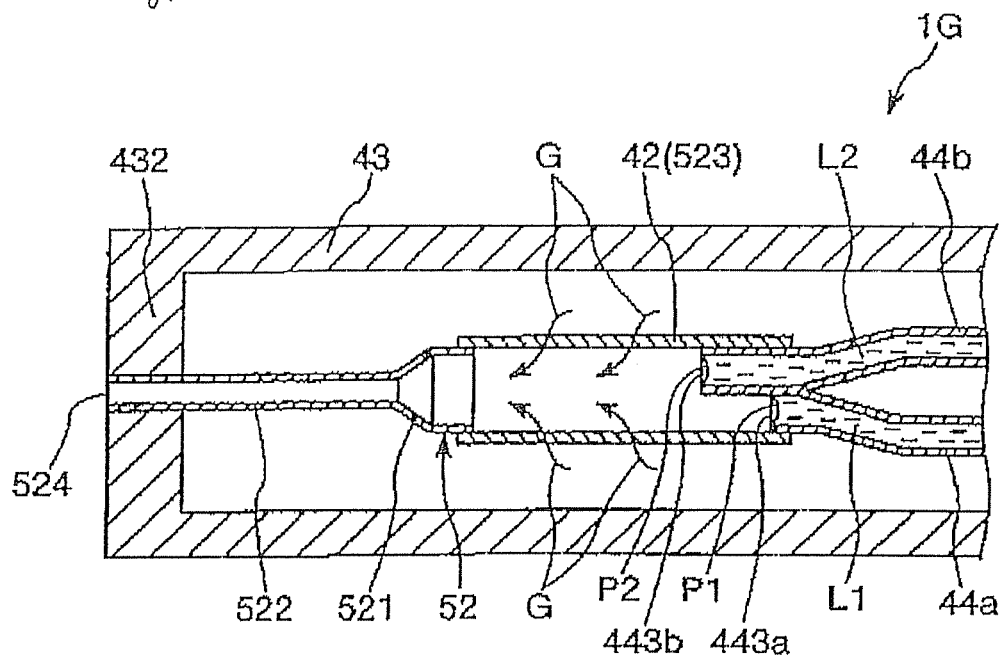
FIG. 25 is a longitudinal cross-sectional view of the distal end part of a nozzle of a sprayer according to an eighth embodiment disclosed here.

In the sprayer 1G shown in FIG. 25, an open end 443a of the first internal tube 44a facing the merge part 52, and an open end 443b of the second internal tube 44b facing the merge part 52 are located at positions misaligned along the longitudinal direction of the nozzle 4 (liquid flow path). That is, the sprayer 1G is configured such that the open end 443b of the second internal tube 44b protrudes distally beyond the open end 443a of the first internal tube 44a and protrudes closer to the distal end than the open end 443a of the first internal tube 44a. Further, the open end 443a of the first internal tube 44a and the open end 443b of the second internal tube 44b are arranged mutually side by side in the diametrical direction of the nozzle 4 (in the vertical direction in FIG. 25).

As described above, upon performing the spray operation of the liquid mixture, and stopping the spray operation, the gas G which has flowed into the merge part 52 by the pressure (residual pressure) in the external tube 43 can blow away the liquid mixture in the merge part 52 from the ejection port 524. This can inhibit or prevent the liquid mixture from remaining in the merge part 52. Accordingly, the liquid mixture is inhibited or prevented from coagulating in the merge part 52, and causing clogging in the ejection port 524. In this embodiment, even when the first liquid L1 unintentionally flows from the open end 443a of the first internal tube 44a into the merge part 52, and the second liquid L2 also unintentionally flows from the open end 443b of the second internal tube 44b into the merge part 52, the flowing first liquid L1 and second liquid L2 can be relatively reliably prevented from being mixed due to the arrangement of the open end 443a and the open end 443b at positions axially offset from one another along the longitudinal direction of the nozzle 4. This inhibits or prevents the two liquids from coagulating in the merge part 52, and from causing clogging in the ejection port 524.

Figure 26:
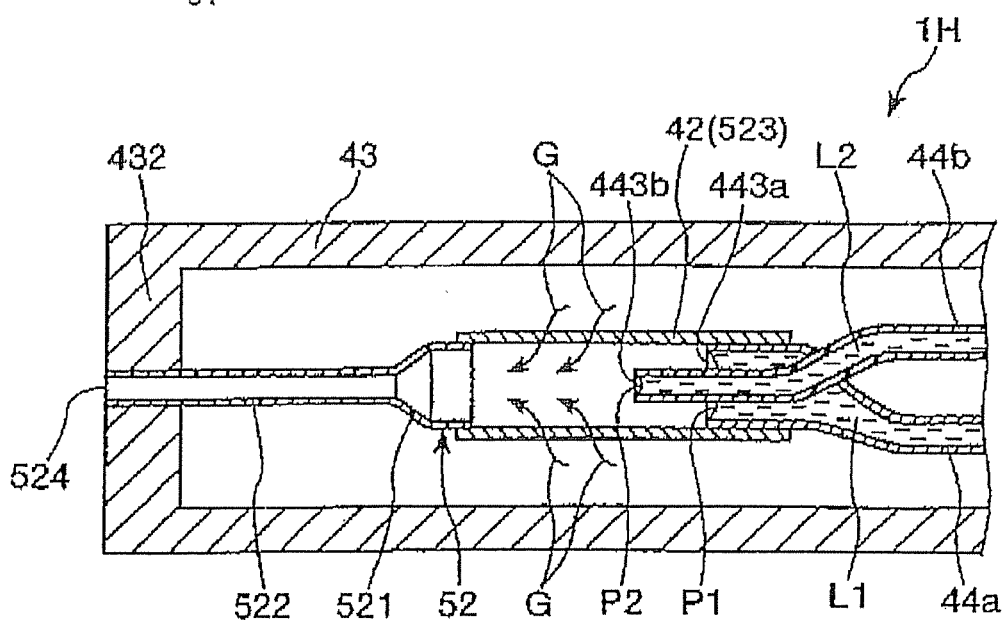
FIG. 26 is a longitudinal cross-sectional view of the distal end part of a nozzle of a sprayer according to a ninth embodiment disclosed here.

FIG. 26 is a longitudinal cross-sectional view of the distal end of a nozzle in a sprayer according to a ninth embodiment. Features in this embodiment that are the same as those in the embodiments described above are designated by the same reference numeral, and a detailed description of such features is not repeated. The description below will primarily describe differences in this embodiment relative to the embodiments described above.

This embodiment is the same as the eighth embodiment, except that the positional relationship of the open ends respectively facing the merge part of respective liquid flow paths is different.

The sprayer 1H shown in FIG. 26 is configured such that the open end 443a of the first internal tube 44a and the open end 443b of the second internal tube 44b are both in the shape of a ring. The open end 443a of the first internal tube 44a surrounds the open end 443b. That is, the open end 443a of the first internal tube 44a and the open end 443b of the second internal tube 44b are disposed concentrically.

With such a configuration, as with the eighth embodiment, even when the first liquid L1 unintentionally flows from the open end 443a of the first internal tube 44a into the merge part 52, and the second liquid L2 also unintentionally flows from the open end 443b of the second internal tube 44b into the merge part 52, the flowing first liquid L1 and second liquid L2 can be relatively reliably inhibited or prevented from being mixed. This inhibits or prevents the two liquids from coagulating in the merge part 52, and from causing clogging in the ejection port 524. With the sprayer 1H, when a spray operation is performed, in the merge part 52, the second liquid L2 from the open end 443b of the second internal tube 44b has a higher flow rate than the flow rate of the first liquid L1 from the open end 443a of the first internal tube 44a.

Up to this point, the sprayer disclosed here have been described by way of the illustrated embodiments. However, the invention is not limited thereto. Respective parts forming each sprayer can be replaced with the parts having a given configuration capable of exhibiting the same or similar functions. Also, given constituents may be added. Further, the sprayer disclosed here may include a combination of two or more configurations (features) from the respective embodiments.

The principles, embodiments and modes of operation of the sprayer have been described in the foregoing specification, but the invention which is intended to be protected is not to be construed as limited to the particular embodiments disclosed. The embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A sprayer comprising:
    a syringe comprising a syringe barrel and a plunger movably positioned in the syringe barrel, the syringe barrel containing a liquid;
    a main body comprised of at least one syringe receiving area for receiving the syringe;
    a user operable operation part operable by the user to move the plunger within the syringe barrel when the syringe is positioned in the syringe receiving area to discharge the liquid from the syringe;
    a nozzle comprising a liquid supply passage possessing an interior along which flows the liquid discharged from the syringe barrel, a gas supply passage connectable to a gas source and possessing an interior along which flows gas from the gas source, and a film separating the interior of the liquid supply passage and the interior of the gas supply passage; and
    the film comprising a plurality of through holes communicating the interior of the gas supply passage to the interior of the liquid supply passage so that gas in the interior of the gas supply passage flows through the through holes in the film and into the interior of the liquid supply passage;
    wherein the liquid supply passage is a liquid supply tube, and the film comprises a plurality of cylindrical films which are axially spaced apart from one another along an axial extent of the liquid supply tube, each of the cylindrical films comprising a plurality of through holes, each of the cylindrical films having opposite ends connected to the liquid supply tube so that the cylindrical films form a part of the liquid supply tube.

2. The sprayer according to claim 1, wherein the liquid supply passage is an internal tube and the gas supply passage is an external tube surrounding the internal tube.

3. The sprayer according to claim 1, wherein the syringe is a first syringe, the liquid in the syringe barrel is a first liquid, the liquid supply passage is a first liquid supply tube, and the film is a first film connected to the first liquid supply tube; further comprising:
    a second syringe comprising a plunger movably positioned in a syringe barrel containing a second liquid different from the first liquid;
    a second liquid supply tube possessing an interior along which flows the second liquid discharged from the syringe barrel of the second syringe, the second liquid supply tube comprising a second film possessing a plurality of through holes allowing the gas in the gas supply tube to flow through the holes in the second film and into the second liquid supply tube.

4. The sprayer according to claim 1, wherein the through holes in the film possess an average pore diameter of 0.45 µm or less.

5. The sprayer according to claim 1, wherein the syringe is a first syringe, the liquid in the syringe barrel is a first liquid, and the liquid supply passage is a first liquid supply tube; further comprising:
    a second syringe comprising a plunger movably positioned in a syringe barrel containing a second liquid different from the first liquid;
    a second liquid supply tube possessing an interior along which flows the second liquid discharged from the syringe barrel of the second syringe; and
    the first liquid supply tube and the second liquid supply tube merging into one another at a merge part at which the first and second liquids are mixed together, the film comprising a cylindrical film at the merge part so that the first and second liquids mix together in the merge part surrounded by the cylindrical film.

6. The sprayer according to claim 1, wherein the syringe is a first syringe, the liquid in the syringe barrel is a first liquid, and the liquid supply passage is a first liquid supply tube; further comprising:
- a second syringe comprising a plunger movably positioned in a syringe barrel containing a second liquid different from the first liquid;
- a second liquid supply tube possessing an interior along which flows the second liquid discharged from the syringe barrel of the second syringe;
- the first liquid supply tube and the second liquid supply tube merging into one another at a merge part at which the first and second liquids are mixed together; and
- the film possessing a tubular shape with a closed end and an open end communicating with the gas supply tube, the closed end of the tubular film being positioned in the merge part.

7. A sprayer comprising:
- a nozzle comprised of a plurality of liquid flow paths through which respective liquids pass, and a gas flow path connectable to a source of gas and along which the gas passes for ejecting the liquids, the nozzle also including an ejection port;
- a first liquid supply connected to one of the liquid flow paths;
- a second liquid supply connected to an other of the liquid flow paths;
- the first and second liquid supplies containing respective liquids different in liquid composition;
- the plurality of liquid flow paths merging together at a merge part so that the first and second liquids mix together within an interior of the merge part;
- a gas permeable film disposed at the merge part, the gas permeable film being impermeable to the liquid, and permeable to the gas in at least a wall part defining the liquid flow path so that the gas introduced into the gas flow path from the gas source flows through the gas permeable film and into the merge part to mix with the first and second liquids, with the gas and the first and second liquids together exiting the nozzle by way of the ejection port.

8. The sprayer according to claim 7, wherein the nozzle comprises a first internal tube forming the one liquid flow paths and a second internal tube forming the other liquid flow path, the first and second internal tubes being located inside an external tube with a gap between an outer circumferential surface of each of the first and second internal tubes and an internal peripheral surface of the external tube, the gap forming the gas flow path.

9. The sprayer according to claim 7, wherein the gas permeable film is situated at a distal end part of the first and second liquid flow paths.

10. The sprayer according to claim 7, wherein the gas permeable film is germ impermeable.

11. The sprayer according to claim 7, wherein the gas permeable film comprises a plurality of pores penetrating through the film in a thickness direction of the film, the pores possessing an average pore diameter of 0.45 µm or less.

12. The sprayer according to claim 7, wherein the gas permeable film is fabricated from a material having hydrophobicity, or is fabricated from a material subjected to a hydrophobization processing.

13. The sprayer according to claim 7, wherein the gas which has passed through the gas permeable film becomes bubbles in the liquids passing through the merge part, and stirs the liquids.

14. The sprayer according to claim 7, wherein the first liquid supply and the second liquid supply are each comprised of a syringe having a syringe external tube, a gasket inserted in the syringe external tube, a plunger for moving and operating the gasket along the longitudinal direction of the syringe external tube, and the respective liquid filled in the space formed by the syringe external tube and the gasket.

15. The sprayer according to claim 7, wherein the liquid supply means comprises a syringe in which a plunger is movably positioned in a syringe barrel possessing an interior, the liquid flow path being in fluid communication with the interior of the syringe barrel so that forward movement of the plunger in the syringe barrel introduces liquid in the interior of the syringe barrel into the liquid flow path.

16. The sprayer according to claim 7, wherein the wall part is a wall part or an inner tube having a lumen constituting the liquid flow path, the inner tube being positioned in an outer tube so that a space exists between an inner surface of the outer tube and an outer surface of the inner tube, the space constituting the gas flow path, the gas permeable film possessing one side facing the space and contactable by the gas, and an opposite side facing the lumen and contactable by the liquid.

17. A sprayer comprising:
- a syringe comprising a syringe barrel and a plunger movably positioned in the syringe barrel, the syringe barrel containing a liquid;
- a main body comprised of at least one syringe receiving area for receiving the syringe;
- a user operable operation part operable by the user to move the plunger within the syringe barrel when the syringe is positioned in the syringe receiving area to discharge the liquid from the syringe;
- a nozzle comprising a liquid supply passage possessing an interior along which flows the liquid discharged from the syringe barrel, a gas supply passage connectable to a gas source and possessing an interior along which flows gas from the gas source, and a film separating the interior of the liquid supply passage and the interior of the gas supply passage so that one side of the film is contactable by the gas and an opposite side of the film is contactable by the liquid, the nozzle possessing an ejection port; and
- the film comprising a plurality of through holes communicating the interior of the gas supply passage to the interior of the liquid supply passage so that gas in the interior of the gas supply passage flows through the through holes in the film and into the interior of the liquid supply passage where the gas mixes with the liquid in the liquid supply passage to form a gas/liquid mixture in the liquid supply passage, the liquid supply passage communicating with the ejection port so that the gas/liquid mixture exits the nozzle by way of the ejection port;
- wherein the syringe is a first syringe, the syringe barrel is a first syringe barrel, the plunger is a first plunger, the liquid is a first liquid, the at least one syringe receiving area is a first syringe receiving area, and the liquid supply passage is a first liquid supply passage; and
- further comprising a second syringe comprising a second syringe barrel and a second plunger movably positioned in the second syringe barrel, the second syringe barrel containing a second liquid which is compositionally different from the first liquid;
- the main body comprising a second syringe receiving area configured to receive the second syringe;
- the user operable operation part being operable by the user to move the second plunger within the second syringe barrel when the second syringe is positioned in the second syringe receiving area to discharge the second liquid from the second syringe; and the nozzle comprising a second liquid supply passage possessing an interior along which flows the second liquid discharged from the second syringe barrel;

wherein the nozzle comprises a merge part, upstream of the ejector port, at which the first and second liquid supply passages merge with one another so that the first and second liquids are mixed together.

18. The sprayer according to claim 17, wherein the film is located at the merge part to permit the gas in the interior of the gas supply passage to flow through the through holes in the film and into the merge part at which the first and second liquids mix so that the gas mixes with the first and second liquids in the merge part.

19. The sprayer according to claim 17, wherein the liquid supply passage possesses a forward end and a distal end, the film possessing a proximal end space distally of the proximal end of the liquid supply passage.

20. A sprayer comprising:

a first syringe comprising a first syringe barrel and a first plunger movably positioned in the first syringe barrel, the first syringe barrel containing a first liquid;

a second syringe comprising a second plunger movably positioned in a second syringe barrel containing a second liquid different from the first liquid;

a main body comprised of at least one syringe receiving area for receiving the first syringe and the second syringe;

a user operable operation part operable by the user to move the first plunger within the first syringe barrel while the first syringe is positioned in the first syringe receiving area to discharge the first liquid from the first syringe and to also move the second plunger within the second syringe barrel while the second syringe is positioned in the second syringe receiving area to discharge the second liquid from the second syringe;

a nozzle comprising a first liquid supply tube possessing an interior along which flows the first liquid discharged from the first syringe barrel, a second liquid supply tube possessing an interior along which flows the second liquid discharged from the second syringe barrel of the second syringe, a gas supply passage connectable to a gas source and possessing an interior along which flows gas introduced into the gas supply passage from the gas source;

the first liquid supply tube and the second liquid supply tube merging together at a merge part possessing an interior at which the first and second liquids are mixed together;

a film at the merge part separating the interior of the merge part and the interior of the gas supply passage, the film comprising a plurality of through holes communicating the interior of the gas supply passage to the interior of the merge part so that gas introduced into the interior of the gas supply passage from the gas source flows through the through holes in the film and into the interior of the merge part to mix with the first and second liquids in the merge part.

* * * * *